US010224200B2

(12) United States Patent
Park et al.

(10) Patent No.: US 10,224,200 B2
(45) Date of Patent: Mar. 5, 2019

(54) ALUMINUM COMPOUND, METHOD OF FORMING THIN FILM BY USING THE SAME, AND METHOD OF FABRICATING INTEGRATED CIRCUIT DEVICE

(71) Applicant: Samsung Electronics Co., Ltd., Suwon-si, Gyeonggi-do (KR)

(72) Inventors: Gyu-hee Park, Hwaseong-si (KR); Jae-soon Lim, Seoul (KR); Youn-joung Cho, Hwaseong-si (KR); Myong-woon Kim, Daejeon (KR); Sang-ick Lee, Daejeon (KR); Sung-duck Lee, Daejeon (KR); Sung-woo Cho, Daegu (KR)

(73) Assignees: Samsung Electronics Co., Ltd., Gyeonggi-do (KR); DNF Co., Ltd., Daejeon (KR)

( * ) Notice: Subject to any disclaimer, the term of this patent is extended or adjusted under 35 U.S.C. 154(b) by 0 days.

(21) Appl. No.: 15/455,879

(22) Filed: Mar. 10, 2017

(65) Prior Publication Data

US 2018/0076024 A1 Mar. 15, 2018

(30) Foreign Application Priority Data

Sep. 13, 2016 (KR) ........................ 10-2016-0118210

(51) Int. Cl.
| | | |
|---|---|---|
| *H01L 21/02* | (2006.01) | |
| *C07F 5/06* | (2006.01) | |
| *C09D 1/00* | (2006.01) | |
| *C09D 5/24* | (2006.01) | |
| *H01L 21/311* | (2006.01) | |
| *H01L 27/11582* | (2017.01) | |

(52) U.S. Cl.
CPC ........ *H01L 21/02178* (2013.01); *C07F 5/062* (2013.01); *C09D 1/00* (2013.01); *C09D 5/24* (2013.01); *H01L 21/0228* (2013.01); *H01L 21/02205* (2013.01); *H01L 21/02321* (2013.01); *H01L 21/31116* (2013.01); *H01L 21/31144* (2013.01); *H01L 27/11582* (2013.01)

(58) Field of Classification Search
CPC ............................................... H01L 21/02178
See application file for complete search history.

(56) References Cited

U.S. PATENT DOCUMENTS

| | | |
|---|---|---|
| 5,468,707 A | 11/1995 | Pohl et al. |
| 5,559,203 A | 9/1996 | Jensen |
| 6,743,475 B2 | 6/2004 | Skarp et al. |
| 7,374,964 B2 | 5/2008 | Ahn et al. |
| 7,488,684 B2 | 2/2009 | Choi et al. |

(Continued)

FOREIGN PATENT DOCUMENTS

| | | |
|---|---|---|
| JP | 5843318 B2 | 1/2016 |
| KR | 10-0756388 B1 | 9/2007 |

(Continued)

OTHER PUBLICATIONS

Schumann J Cry Growth vol. 107 Jan. 1991 p. 309-313 (Year: 1991).*

*Primary Examiner* — Joseph A Miller, Jr.
(74) *Attorney, Agent, or Firm* — Harness, Dickey & Pierce, P.L.C.

(57) ABSTRACT

An aluminum compound is represented by Chemical Formula (I) and is used as a source material for forming an aluminum-containing thin film.

8 Claims, 30 Drawing Sheets

(56) References Cited

U.S. PATENT DOCUMENTS

| | | |
|---|---|---|
| 7,985,450 B2 | 7/2011 | Shin et al. |
| 8,268,397 B2 | 9/2012 | Cho et al. |
| 8,835,273 B2 | 9/2014 | Chen et al. |
| 8,927,059 B2 | 1/2015 | Lu et al. |
| 9,194,041 B2 | 11/2015 | Shirai et al. |
| 9,255,324 B2 | 2/2016 | Koh et al. |
| 2005/0239297 A1 | 10/2005 | Senzaki et al. |
| 2014/0242263 A1 | 8/2014 | Youn et al. |
| 2015/0146341 A1 | 5/2015 | Fuchigami et al. |
| 2015/0255276 A1 | 9/2015 | Cho et al. |

FOREIGN PATENT DOCUMENTS

| | | |
|---|---|---|
| KR | 2014/0136146 A | 11/2014 |
| KR | 2016/0082321 A | 7/2016 |

\* cited by examiner

ALUMINUM COMPOUND, METHOD OF FORMING THIN FILM BY USING THE SAME, AND METHOD OF FABRICATING INTEGRATED CIRCUIT DEVICE

CROSS-REFERENCE TO RELATED APPLICATION

This application claims the benefit of Korean Patent Application No. 10-2016-0118210, filed on Sep. 13, 2016, in the Korean Intellectual Property Office, the disclosure of which is incorporated herein in its entirety by reference.

BACKGROUND

1. Field

Example embodiments of the inventive concepts relate to an aluminum compound, a method of forming a thin film using the same, and/or a method of fabricating an integrated circuit device, and more particularly, to an aluminum compound, which is a liquid at room temperature, a method of forming a thin film using the same, and/or a method of fabricating an integrated circuit device.

2. Description of the Related Art

Due to the development of electronic technology, downscaling of semiconductor devices is being quickly performed in recent years, and thus, structures of patterns constituting electronic devices are becoming more complicated and finer. Along with this, there is a need to develop a raw material compound capable of forming an aluminum-containing thin film to a uniform thickness on a complicated and fine 3-dimensional structure by securing thermal stability upon the formation of the aluminum-containing thin film.

SUMMARY

Example embodiments of the inventive concepts provide an aluminum heterocyclic compound capable of having improved step coverage, thermal stability, and relatively high volatility and providing improved process stability and mass productivity, upon the formation of an aluminum-containing thin film using the aluminum heterocyclic compound as a source material.

Example embodiments of the inventive concepts also provide a method of forming an aluminum-containing thin film, which can provide improved step coverage, process stability, and mass productivity, and a method of fabricating an integrated circuit device, which can provide improved electrical properties.

According to example embodiments of the inventive concepts, an aluminum compound is represented by Chemical Formula (I):

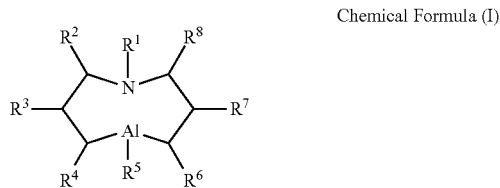

Chemical Formula (I)

wherein each of $R^1$, $R^2$, $R^3$, $R^4$, $R^5$, $R^6$, $R^7$, and $R^8$ are independently a hydrogen atom, a halogen atom, a $C_1$ to $C_7$ substituted or unsubstituted alkyl group, a $C_2$ to $C_7$ substituted or unsubstituted alkenyl group, a $C_2$ to $C_7$ substituted or unsubstituted alkynyl group, or a $C_4$ to $C_{20}$ substituted or unsubstituted aromatic or alicyclic hydrocarbon group.

According to example embodiments of the inventive concepts, a method of forming a thin film includes forming an aluminum-containing film on a substrate using the aluminum compound represented by Chemical Formula (I).

According to example embodiments of the inventive concepts, a method of fabricating an integrated circuit device includes forming a lower structure on a substrate, and forming an aluminum-containing film on the lower structure at a temperature of about 300° C. to about 600° C. using the aluminum compound represented by Chemical Formula (I).

According to example embodiments of the inventive concepts, a method of forming a thin film includes forming an aluminum-containing film on a substrate using a heterocyclic precursor including aluminum and nitrogen, the heterocyclic precursor including a heterocyclic ring having more than two carbon atoms.

According to example embodiments of the inventive concepts, because the aluminum heterocyclic compound is in a liquid state at room temperature and has improved thermal stability and relatively high volatility, handling and transfer of the aluminum heterocyclic compound is facilitated. Therefore, the aluminum heterocyclic compound is suitable to be used as a thin film-forming material for fabricating a highly integrated circuit device. In addition, because the aluminum heterocyclic compound suppresses foreign substances (e.g., carbon residues remaining in a thin film), an aluminum-containing film of improved quality can be obtained. According to example embodiments of the inventive concepts, an aluminum-containing film of improved quality can be formed using process conditions having an advantage in terms of process stability and mass productivity, and an integrated circuit device capable of providing improved electrical properties can be fabricated using the aluminum-containing film.

BRIEF DESCRIPTION OF THE DRAWINGS

Example embodiments of the inventive concepts will be more clearly understood from the following detailed description taken in conjunction with the accompanying drawings in which:

FIG. 7A is a plan view of an integrated circuit device, FIG. 7B is a perspective view of the integrated circuit device of FIG. 7A, and FIG. 7C shows cross-sectional views of the integrated circuit device, which are respectively taken along lines X-X' and Y-Y' of FIG. 7A;

DETAILED DESCRIPTION

Figure 1:
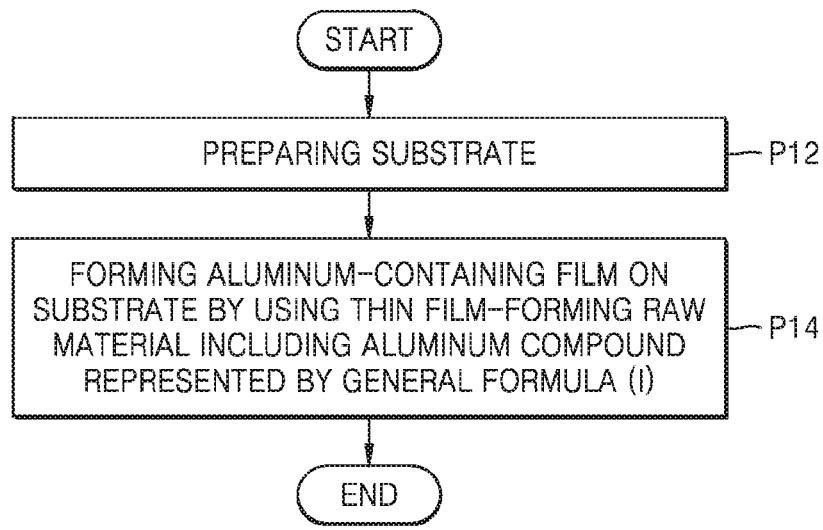
FIG. 1 is a flowchart of a method of forming a thin film, according to example embodiments of the inventive concepts.

Hereinafter, example embodiments of the inventive concepts will be described in detail with reference to the accompanying drawings. Like components will be denoted by like reference numerals throughout the specification, and repeated descriptions thereof will be omitted. As used herein, the term "room temperature" refers to a temperature ranging from about 20° C. to about 28° C. and may vary with the seasons.

According to example embodiments of the inventive concepts, an aluminum heterocyclic compound includes aluminum and nitrogen, and a heterocyclic ring of the aluminum heterocyclic compound has more than two carbon atoms. For example, the aluminum heterocyclic compound may be represented by Chemical Formula (I):

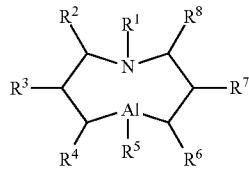

wherein each of $R^1$, $R^2$, $R^3$, $R^4$, $R^5$, $R^6$, $R^7$, and $R^8$ are independently a hydrogen atom, a halogen atom, a $C_1$ to $C_7$ substituted or unsubstituted alkyl group, a $C_2$ to $C_7$ substituted or unsubstituted alkenyl group, a $C_2$ to $C_7$ substituted or unsubstituted alkynyl group, or a $C_4$ to $C_{20}$ substituted or unsubstituted aromatic or alicyclic hydrocarbon group.

In example embodiments, at least some of $R^1$, $R^2$, $R^3$, $R^4$, $R^5$, $R^6$, $R^7$, and $R^8$ may be hydrocarbon groups substituted with halogen atoms, for example, fluorine atoms. In example embodiments, each of $R^1$, $R^2$, $R^3$, $R^4$, $R^5$, $R^6$, $R^7$, and $R^8$ may be a functional group exclusively containing carbon and hydrogen atoms. The alkyl group set forth above may be a linear, branched, or cyclic alkyl group. Examples of the linear alkyl group may include a methyl group, an ethyl group, a propyl group, a butyl groups, etc., without being limited thereto. Examples of the branched alkyl group may include a t-butyl group, without being limited thereto. Examples of the cyclic alkyl group may include a cyclopropyl group, a cyclopentyl group, a cyclohexyl group, etc., without being limited thereto.

The aluminum heterocyclic compound represented by Chemical Formula (I) may have a thermal decomposition temperature of about 350° C. to about 550° C.

An aluminum-containing film is used for various purposes in semiconductor devices, and the reliability of semiconductor devices may depend upon film properties of an aluminum-containing film. For example, when an aluminum oxide film is formed by an atomic layer deposition (ALD) process, an aluminum heterocyclic compound used as an aluminum precursor needs to be vaporized. In addition, to form an aluminum oxide film having improved thin film properties, an ALD process temperature needs to be set relatively high. Here, if the aluminum heterocyclic compound used as the aluminum precursor has relatively low thermal stability, the aluminum heterocyclic compound may be thermally decomposed during the ALD process performed at a relatively high temperature, for example, a temperature of about 400° C. or more. As a result, instead of self-limiting reaction required for ALD, chemical vapor deposition (CVD) may primarily occur. Thus, an aluminum oxide film having desirable film properties is not obtained. If the temperature upon the ALD process is set relatively low in order to inhibit or prevent such a problem, a thin film does not have improved quality free from impurities and does not satisfy step coverage required in the case of a relatively high aspect ratio.

The aluminum heterocyclic compound according to example embodiments of the inventive concepts has a relatively high thermal decomposition temperature of about 350° C. to about 550° C. Thus, ALD deposition properties may be satisfied even though an ALD process is performed at a temperature of about 400° C. or more using the aluminum heterocyclic compound according to example embodiments of the inventive concepts. In addition, an aluminum-containing film may be formed by a relatively high temperature process, and as a result, undesirable impurities may be reduced or prevented from remaining in the obtained aluminum-containing film. Therefore, the aluminum-containing film can exhibit improved film properties and improved step coverage even in the case of a relatively high aspect ratio.

In addition, the aluminum heterocyclic compound according to example embodiments of the inventive concepts exhibits sufficient volatility to perform an ALD process, and is in a liquid state at room temperature due to a relatively low melting point thereof. Therefore, when the aluminum heterocyclic compound is used in a fabrication process of an integrated circuit device, the aluminum heterocyclic compound is easily handled and is suitable as a thin film-forming raw material by ALD.

In example embodiments, in Chemical Formula (I), each of $R^1$ and $R^5$ may independently be a $C_1$ to $C_7$ alkyl group, and each of $R^2$, $R^3$, $R^4$, $R^6$, $R^7$, and $R^8$ may independently be a hydrogen atom or a $C_1$ to $C_7$ alkyl group.

In example embodiments, the aluminum heterocyclic compound according to example embodiments of the inventive concepts may be represented by Chemical Formula (II):

Chemical Formula (II)

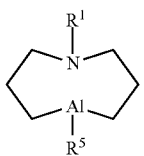

wherein each of $R^1$ and $R^5$ are independently a $C_1$ to $C_7$ alkyl group. For example, the aluminum heterocyclic compound according to example embodiments of the inventive concepts may be represented by Chemical Formula (1).

Chemical Formula (1)

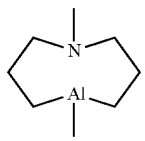

FIG. 1 is a flowchart of a method of forming a thin film, according to example embodiments of the inventive concepts.

In a process P12 of FIG. 1, a substrate is prepared.

In a process P14 of FIG. 1, an aluminum-containing film is formed on the substrate using a thin film-forming raw material including an aluminum heterocyclic compound represented by Chemical Formula (I). In example embodiments, the aluminum heterocyclic compound included in the thin film-forming raw material used in the process P14 may be a liquid at room temperature. In example embodiments, the aluminum heterocyclic compound used in the process P14 may have a thermal decomposition temperature of about 350° C. to about 550° C. In example embodiments, the aluminum heterocyclic compound may have a structure represented by Chemical Formula (1).

In example embodiments, the thin film-forming raw material may include at least one of aluminum heterocyclic compounds according to example embodiments of the inventive concepts and may not include other metal compounds and semimetal compounds. In example embodiments, the thin film-forming raw material may include a compound (referred to by the term "another precursor" hereinafter) including a desirable metal or semimetal, in addition to the aluminum heterocyclic compound according to example embodiments of the inventive concepts. In example embodiments, the thin film-forming raw material may include an organic solvent or a nucleophilic reagent in addition to the aluminum heterocyclic compound according to example embodiments of the inventive concepts.

Examples of the other precursor capable of being used in the method of forming a thin film may include at least one Si or metal compound including one of hydride, hydroxide, halide, azide, alkyl, alkenyl, cycloalkyl, allyl, alkynyl, amino, dialkylaminoalkyl, monoalkylamino, dialkylamino, diamino, di(silyl-alkyl)amino, di(alkyl-silyl)amino, disilylamino, alkoxy, alkoxyalkyl, hydrazide, phosphide, nitrile, dialkylaminoalkoxy, alkoxyalkyldialkylamino, siloxy, diketonate, cyclopentadienyl, silyl, pyrazolate, guanidinate, phosphoguanidinate, amidinate, ketoiminate, diketoiminate, carbonyl, and phosphoamidinate groups as ligands.

A metal included in the other precursors, which may be used as the thin film-forming raw material in the method of forming a thin film according to example embodiments of the inventive concepts, may include Ti, Ta, Mg, Ca, Sr, Ba, Ra, Sc, Y, Zr, Hf, V, Nb, Cr, Mo, W, Mn, Fe, Os, Co, Rh, Ir, Ni, Pd, Pt, Cu, Ag, Au, Zn, Cd, Ga, In, Ge, Sn, Pb, Sb, Bi, La, Ce, Pr, Nd, Pm, Sm, Eu, Gd, Tb, Dy, Ho, Er, Tm, Yb, etc. However, the inventive concepts are not limited to the metals set forth above as examples.

The thin film-forming raw material including the aluminum heterocyclic compound according to example embodiments of the inventive concepts may be suitably used for an ALD process, and the aluminum heterocyclic compound according to example embodiments of the inventive concepts may be used as an Al precursor required for an ALD process in a process of forming a thin film used in the fabrication of an integrated circuit device.

In the method of forming a thin film, according to example embodiments of the inventive concepts, the aluminum-containing film may be formed in a reaction chamber of a deposition apparatus using the aluminum heterocyclic compound represented by Chemical Formula (I). For example, to form the aluminum-containing film, the aluminum heterocyclic compound may be supplied into the reaction chamber maintained at a temperature of about 300° C. to about 600° C. The reaction chamber may be maintained at a pressure of about 10 Pa to atmospheric pressure. In example embodiments, to form the aluminum-containing film, the aluminum heterocyclic compound may be supplied alone onto the substrate. In example embodiments, to form the aluminum-containing film, a multi-component raw material, which includes a mixture of the aluminum heterocyclic compound and at least one of a precursor compound, a reactive gas, and an organic solvent, may be supplied onto the substrate, the precursor compound including a metal that is different from aluminum. The time for supplying the gases into the reaction chamber once may range from about 0.1 seconds to about 100 seconds.

When an aluminum nitride film is formed by the method of forming a thin film, according to example embodiments of the inventive concepts, the reactive gas may be selected from among $NH_3$, monoalkylamines, dialkylamines, trialkylamines, organic amine compounds, hydrazine compounds, and combinations thereof.

When an aluminum oxide film is formed by the method of forming a thin film, according to example embodiments of the inventive concepts, the reactive gas may be an oxidative gas selected from among $O_2$, $O_3$, plasma $O_2$, $H_2O$, $NO_2$, NO, $N_2O$ (nitrous oxide), $CO_2$, $H_2O_2$, HCOOH, $CH_3COOH$, $(CH_3CO)_2O$, and combinations thereof.

In example embodiments, the reactive gas may be a reductive gas, for example, $H_2$.

The aluminum heterocyclic compound and the reactive gas may be simultaneously or sequentially supplied onto the substrate.

In the method of forming a thin film, according to example embodiments of the inventive concepts, the substrate for forming a thin film may include a silicon substrate, a ceramic substrate (e.g., SiN, TiN, TaN, TiO, RuO, ZrO, HfO, or LaO), a glass substrate, a metal substrate (e.g., ruthenium), etc.

Figure 2:
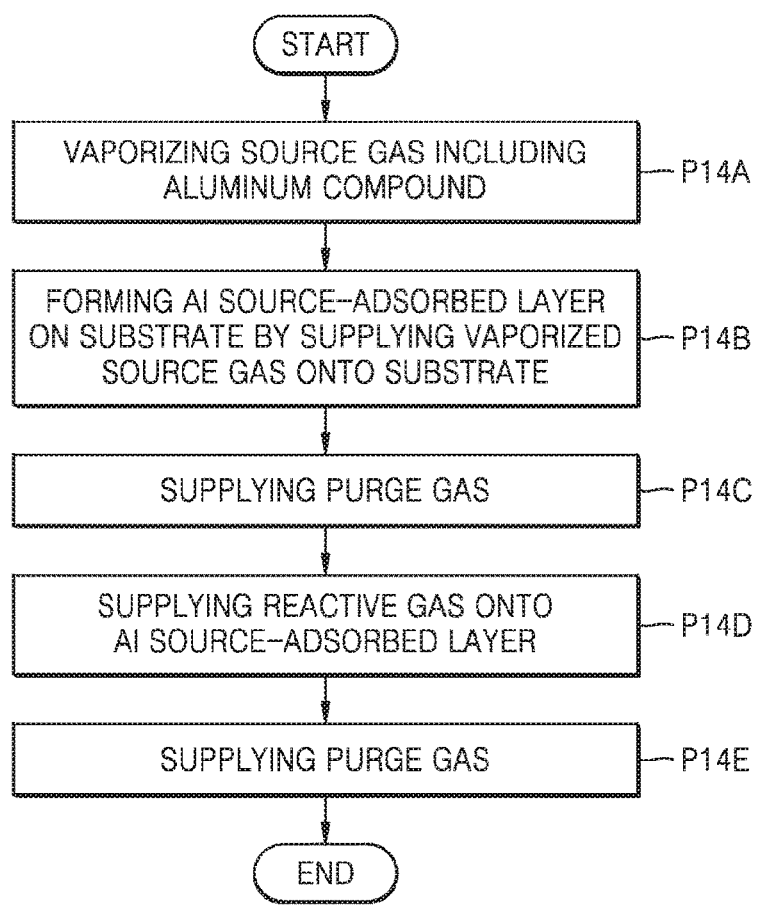
FIG. 2 is a flowchart of an example method of forming an aluminum-containing film, according to example embodiments of the inventive concepts.

FIG. 2 is a flowchart of an example method of forming an aluminum-containing film, according to example embodiments of the inventive concepts. The method of forming the aluminum-containing film by an ALD process, according to the process P14 of FIG. 1, will be described in more detail with reference to FIG. 2.

Referring to FIG. 2, in a process P14A, a source gas including an aluminum heterocyclic compound is vaporized.

The aluminum heterocyclic compound may include the aluminum heterocyclic compound represented by Chemical Formula (I).

In a process P14B, an Al source-adsorbed layer is formed on the substrate by supplying the vaporized source gas obtained according to the process P14A onto the substrate while maintaining an inside of a chamber at a temperature of about 300° C. to about 600° C. The Al source-adsorbed layer including a chemisorbed layer and a physisorbed layer of the source gas may be formed on the substrate by supplying the vaporized source gas onto the substrate.

In a process P14C, undesirable byproducts on the substrate are removed by supplying a purge gas onto the substrate while maintaining the inside of the chamber at a temperature of about 300° C. to about 600° C. The purge gas may include, for example, an inert gas, e.g., Ar, He, or Ne, $N_2$ gas, etc.

In a process P14D, a reactive gas is supplied onto the Al source-adsorbed layer formed on the substrate while maintaining the inside of the chamber at a temperature of about 300° C. to about 600° C.

When an aluminum nitride film is formed as the aluminum-containing film, the reactive gas may be one of $NH_3$, monoalkylamines, dialkylamines, trialkylamines, organic amine compounds, hydrazine compounds, and combinations thereof. When an aluminum oxide film is formed as the aluminum-containing film, the reactive gas may be an oxidative gas including one of $O_2$, $O_3$, plasma $O_2$, $H_2O$, $NO_2$, NO, $N_2O$, $CO_2$, $H_2O_2$, HCOOH, $CH_3COOH$, $(CH_3CO)_2O$, and combinations thereof. In example embodiments, the reactive gas may be a reductive gas, for example, $H_2$.

In a process P14E, undesirable byproducts on the substrate are removed by supplying a purge gas onto the substrate.

After the process P14E is performed, a process of annealing the aluminum-containing film may be performed. The annealing may be performed at a temperature that is higher than the process temperature used in the processes P14B to P14E. For example, the annealing may be performed at a temperature selected from a range of about 500° C. to about 1150° C. In example embodiments, the annealing may be performed in a nitrogen atmosphere. As described above, the annealing process is performed, whereby the aluminum-containing film may be densified, and may exhibit improved film properties by removal of impurities in the aluminum-containing film. For example, when an aluminum oxide film is formed as the aluminum-containing film by the processes of FIG. 2, the aluminum oxide film may be shrunk due to densification thereof by the annealing process, and thus may have increased density.

The method of forming the aluminum-containing film, which has been described with reference to FIG. 2, is merely an example, and various modifications and changes of the method can be made without departing from the spirit and scope of example embodiments of the inventive concepts.

To form the aluminum-containing film on the substrate by the method of forming a thin film, according to example embodiments of the inventive concepts, the aluminum heterocyclic compound represented by Chemical Formula (I), and at least one of another precursor, a reactive gas, a carrier gas, and a purge gas may be simultaneously or sequentially supplied onto the substrate. In example embodiments, the aluminum heterocyclic compound may be represented by Chemical Formula (II), and here, each of $R^1$ and $R^5$ may independently be a $C_1$ to $C_7$ alkyl group. For example, the aluminum heterocyclic compound may be represented by Chemical Formula (1).

According to example embodiments of the inventive concepts, when the aluminum-containing film is formed by an ALD process, the number of ALD cycles may be adjusted in order to control the aluminum-containing film to a desirable thickness.

For example, when the aluminum-containing film is formed by an ALD process, energy (e.g., plasma, light, voltage, etc.) may be applied. A time point for applying the energy may be variously selected. For example, the time point for applying the energy may be a time point at which the source gas including the aluminum heterocyclic compound is introduced into the reaction chamber, a time point at which the source gas is adsorbed onto the substrate, a time point at which an exhaust process is performed using the purge gas, a time point at which the reactive gas is introduced into the reaction chamber, or between these time points, the energy (e.g., plasma, light, voltage, etc.) may be applied.

The method of forming a thin film, according to example embodiments of the inventive concepts, may further include a process of annealing the aluminum-containing film in an inert, oxidative, or reductive atmosphere, after the aluminum-containing film is formed using the aluminum heterocyclic compound represented by Chemical Formula (I). In addition, to fill a step formed on a surface of the aluminum-containing film, the method of forming a thin film may further include a process of reflowing the aluminum-containing film, as needed. Each of the annealing process and the reflow process may be performed at a temperature selected from a range of about 200° C. to about 1150° C., without being limited thereto.

According to the method of forming a thin film, the aluminum heterocyclic compound according to example embodiments of the inventive concepts, the other precursor used together with the aluminum heterocyclic compound, the reactive gas, and the conditions for forming a thin film may be appropriately selected, thereby forming various aluminum-containing films.

In example embodiments, the aluminum-containing film formed by the method of forming a thin film, according to example embodiments of the inventive concepts, may include an aluminum oxide film represented by $Al_2O_3$, an aluminum nitride film represented by AN, an aluminum alloy film, a composite oxide film including an aluminum alloy, etc. In example embodiments, the composite oxide film may include a carbon atom. The carbon atom included in the composite oxide film may be derived from a carbon atom included in the aluminum heterocyclic compound represented by Chemical Formula (I). Although the composite oxide film may include a composite oxide film of Ti and Al, a composite oxide film of Ta and Al, etc., the inventive concepts are not limited to the examples set forth above.

The aluminum-containing film fabricated by the method of forming a thin film, according to example embodiments of the inventive concepts, may be used for various purposes. For example, the aluminum-containing film may be used for a tunnel barrier of a gate dielectric film included in a 3-dimentional charge trap flash (CTF) cell, a gate of a transistor, a conductive barrier film included in a metal wire (e.g., a copper wire), a dielectric film of a capacitor, a barrier metal film for liquid crystals, a member for thin film solar cells, a member for semiconductor equipment, a nanostructure, etc., without being limited thereto.

FIGS. 3A to 3H are cross-sectional views illustrating sequential processes of fabricating an integrated circuit device, according to example embodiments of the inventive concepts. A method of fabricating a memory cell array of an integrated circuit device 100 (see FIG. 3H) constituting a vertical non-volatile memory device will be described with reference to FIGS. 3A to 3H.

Figure 3A:
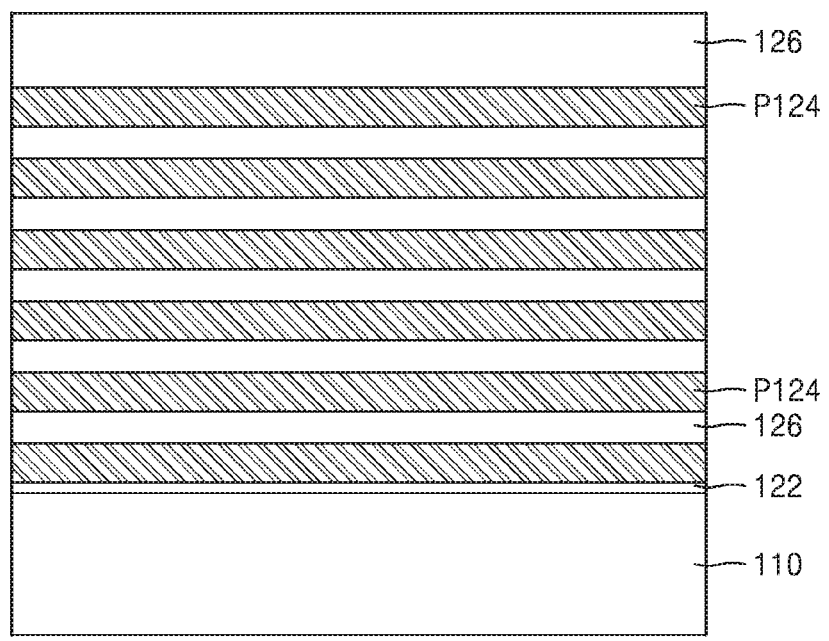
FIGS. 3A to 3H are cross-sectional views illustrating sequential processes of fabricating an integrated circuit device, according to example embodiments of the inventive concepts.

Referring to FIG. 3A, an etch stop insulating film 122 is formed on a substrate 110, and a plurality of sacrificial layers P124 and a plurality of insulating layers 126 are alternately stacked on the etch stop insulating film 122, layer by layer. A thickness of the uppermost insulating layer 126 may be greater than a thickness of another insulating layer 126.

The substrate 110 may include a semiconductor (e.g., Si or Ge), or a compound semiconductor (e.g., SiC, GaAs, InAs, or InP). The substrate 110 may include a semiconductor substrate and structures including at least one insulating film or at least one conductive region on the semiconductor substrate.

The etch stop insulating film 122 and the plurality of insulating layers 126 may include an insulating material, for example, silicon oxide. The plurality of sacrificial layers P124 may include a material having etch selectivity that is different from those of the etch stop insulating film 122 and the plurality of insulating layers 126. For example, the plurality of sacrificial layers P124 may include a silicon nitride film, a silicon oxynitride film, a polysilicon film, or a polysilicon germanium film.

Figure 3B:
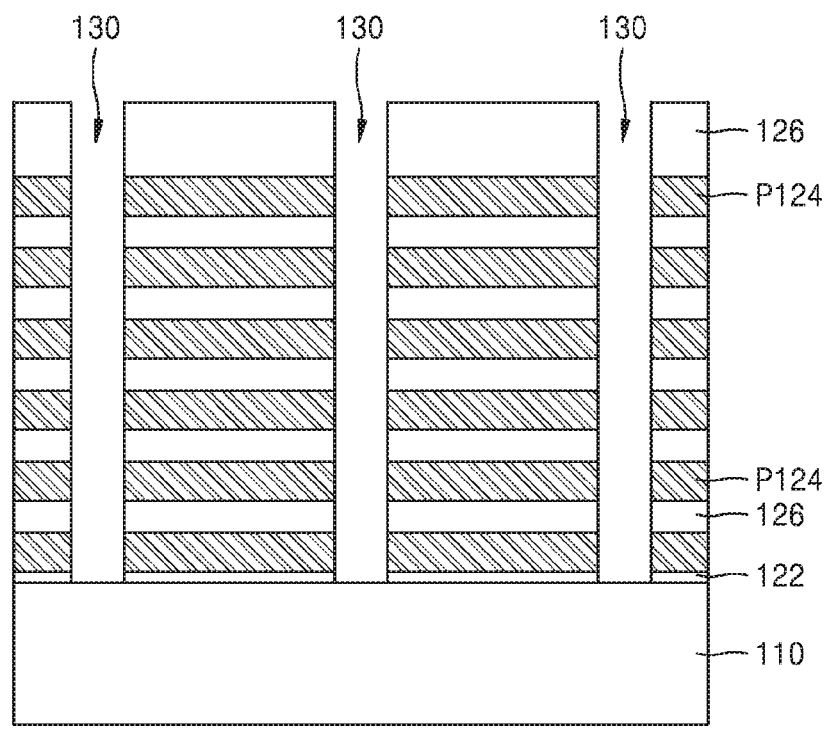

Referring to FIG. 3B, a plurality of channel holes 130 are formed through the plurality of insulating layers 126, the plurality of sacrificial layers P124, and the etch stop insulating film 122 and expose the substrate 110.

Figure 3C:
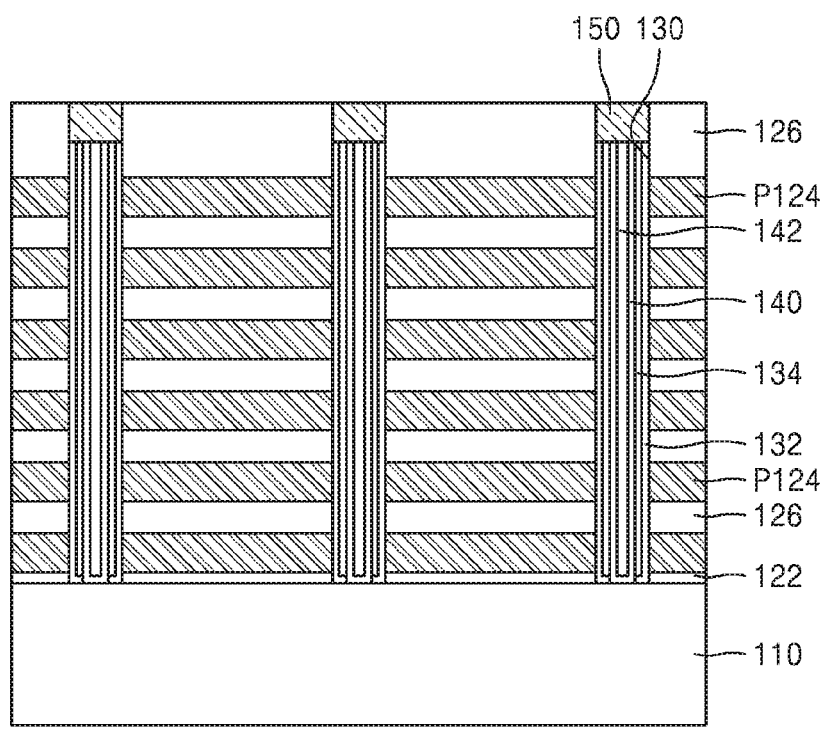

Referring to FIG. 3C, a charge storage film 132 and a tunnel dielectric film 134 are formed in this stated order and cover an inner wall of each of the plurality of channel holes 130, and a channel region 140 is formed and covers the tunnel dielectric film 134.

The charge storage film 132 may include a silicon nitride film. The tunnel dielectric film 134 may include a silicon oxide film. The channel region 140 may include a semiconductor layer, for example, a Si layer. The channel region 140 may not completely fill an inside of each channel hole 130. An insulating film 142 may fill a space remaining above the channel region 140 in each channel hole 130.

The charge storage film 132, the tunnel dielectric film 134, the channel region 140, and the insulating film 142 in the plurality of channel holes 130 are partially removed, whereby an upper space is formed in each of the plurality of channel holes 130, and a conductive pattern 150 may fill the upper space in each of the plurality of channel holes 130. The conductive pattern 150 may include doped polysilicon. The conductive pattern 150 may be used as a drain region.

Figure 3D:
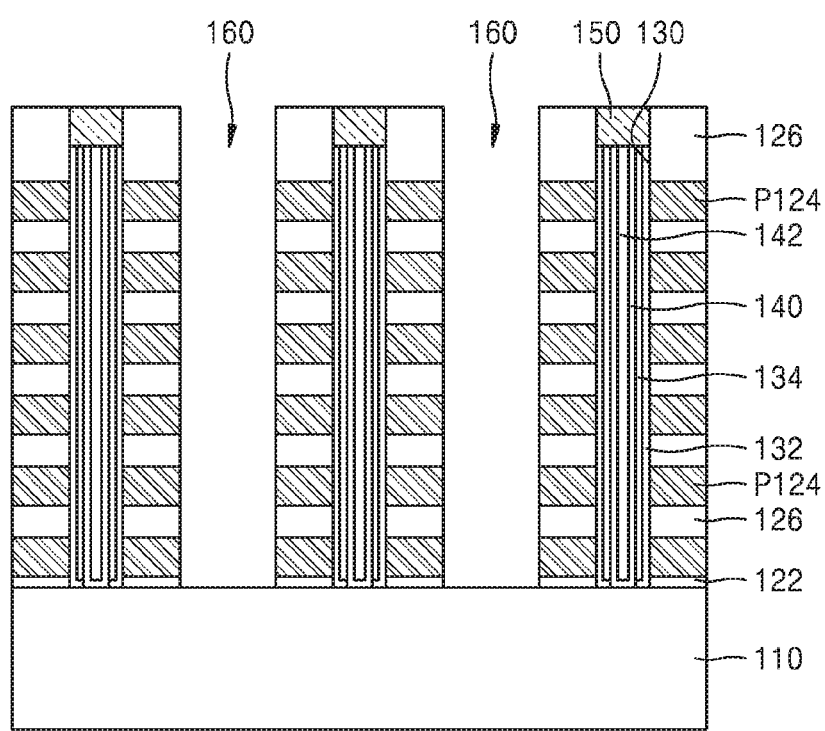

Referring to FIG. 3D, a plurality of openings 160 are formed through the plurality of insulating layers 126, the plurality of sacrificial layers P124, and the etch stop insulating film 122 and expose the substrate 110.

Each of the plurality of openings 160 may be a word line cut region.

Figure 3E:
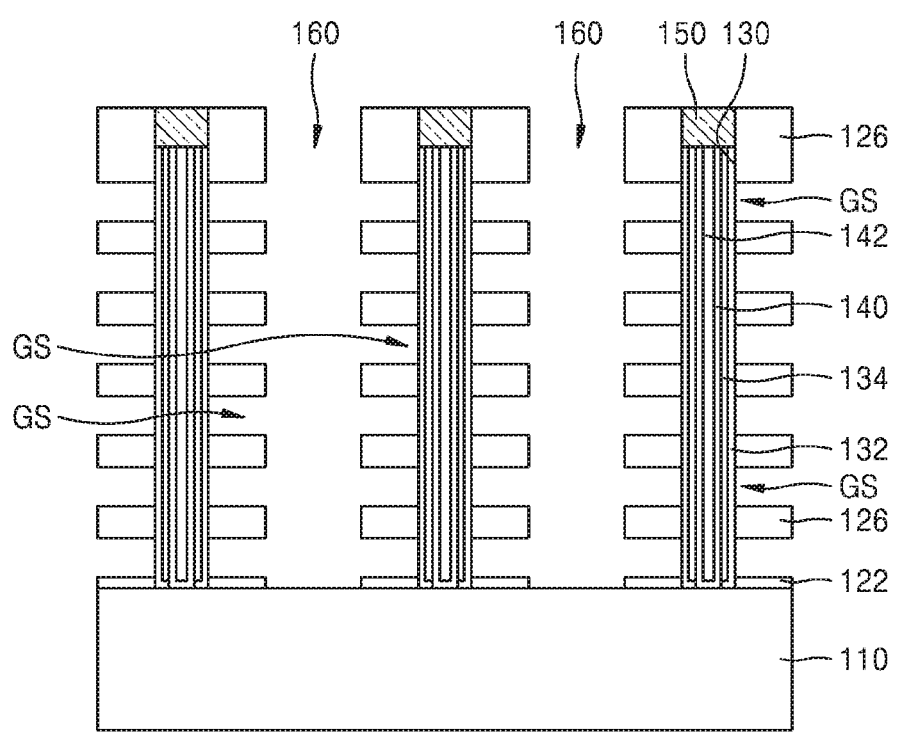

Referring to FIG. 3E, the plurality of sacrificial layers P124 are removed from the plurality of openings 160, thereby forming a plurality of gate spaces GS each between two of the plurality of insulating layers 126. The charge storage film 132 may be exposed by the plurality of gate spaces GS.

Figure 3F:
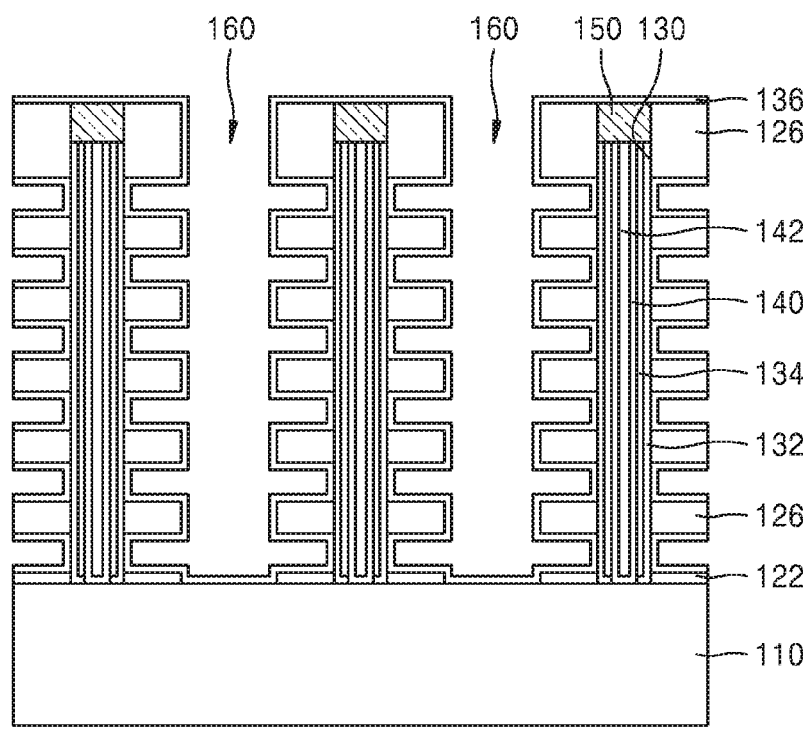

Referring to FIG. 3F, a blocking insulating film 136 is formed and covers inner walls of the plurality of gate spaces GS.

The blocking insulating film 136 may include an aluminum oxide film. To form the blocking insulating film 136, the method of forming a thin film may be used, the method having been described with reference to FIG. 1 or 2. In example embodiments, to form the blocking insulating film 136, an ALD process may be used. Here, as an Al source, the aluminum heterocyclic compound represented by Chemical Formula (I), for example, the aluminum heterocyclic compound represented by Chemical Formula (1), may be supplied through the plurality of openings 160. The ALD process may be performed at a first temperature selected from a range of about 300° C. to about 600° C. After the formation of the aluminum oxide film, the aluminum oxide film may be densified by annealing the aluminum oxide film at a second temperature that is higher than the first temperature. The second temperature may be selected from a range of about 500° C. to about 1150° C.

Figure 3G:
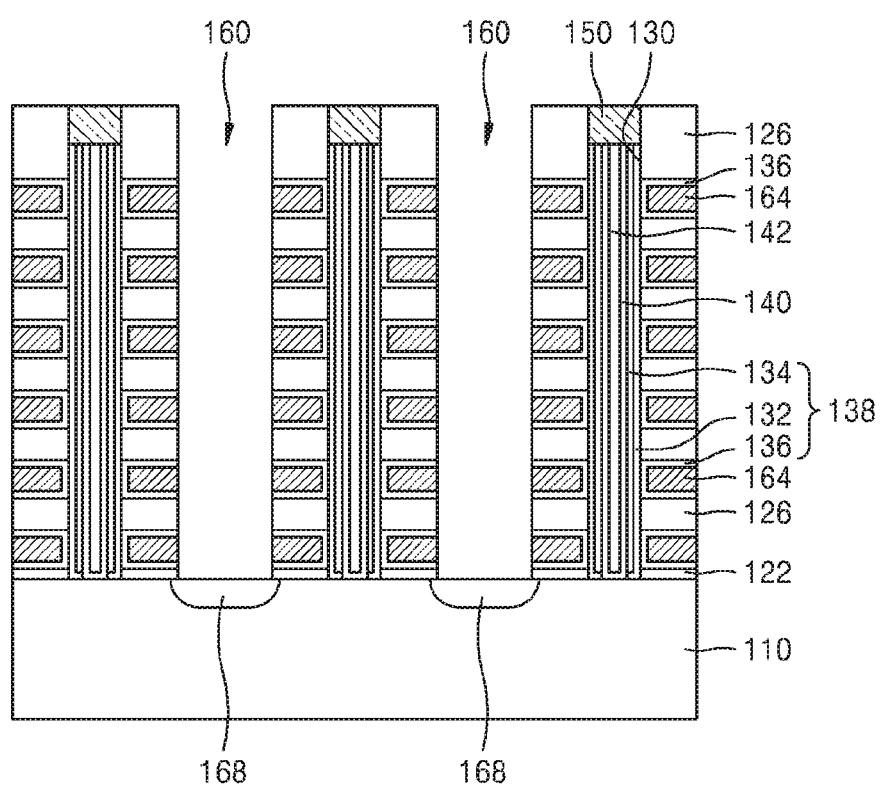

Referring to FIG. 3G, a conductive layer for gate electrodes is formed and fills spaces surrounded by the blocking insulating film 136 and remaining in the plurality of gate spaces GS, followed by partially removing the blocking insulating film 136 and the conductive layer for gate electrodes such that a sidewall of each of the plurality of insulating layers 126 in the plurality of openings 160 is exposed, whereby the blocking insulating film 136 and a gate electrode 164 remain in the plurality of openings 160.

The tunnel dielectric film 134, the charge storage film 132, and the blocking insulating film 136, which are formed on the channel region 140 in this stated order and formed between the channel region 140 and the gate electrode 164, may constitute a gate dielectric film 138.

In example embodiments, the gate electrode 164 may include a first conductive barrier film contacting the blocking insulating film 136, and a first conductive film on the first conductive barrier film. The first conductive barrier film may include a conductive metal nitride, for example, TiN or TaN. The first conductive film may include conductive polysilicon, a metal, a metal silicide, or combinations thereof.

The blocking insulating film 136 may include an aluminum oxide film free from undesirable foreign substances, e.g., carbon residue. As described with reference to FIG. 3F, the aluminum oxide film is annealed and thus densified, thereby reducing or preventing problems (e.g., damage of a constitution material of the gate electrode 164 filling the gate spaces GS) because an excess of the blocking insulating film 136 is consumed due to excessive exposure to an etching atmosphere or the blocking insulating film 136 at entrance sides of the plurality of gate spaces GS is subjected to undesirable removal due to an etching atmosphere, while the blocking insulating film 136 and the conductive layer for gate electrodes are partially removed in the process of FIG. 3G such that the sidewall of each of the plurality of insulating layers 126 is exposed.

After the blocking insulating film 136 and the gate electrode 164 remain only in each of the plurality of gate spaces GS, the substrate 110 may be exposed by the plurality of openings 160. A plurality of common source regions 168 may be formed in the substrate 110 by implanting impurities into the substrate 110 exposed by the plurality of openings 160.

Figure 3H:
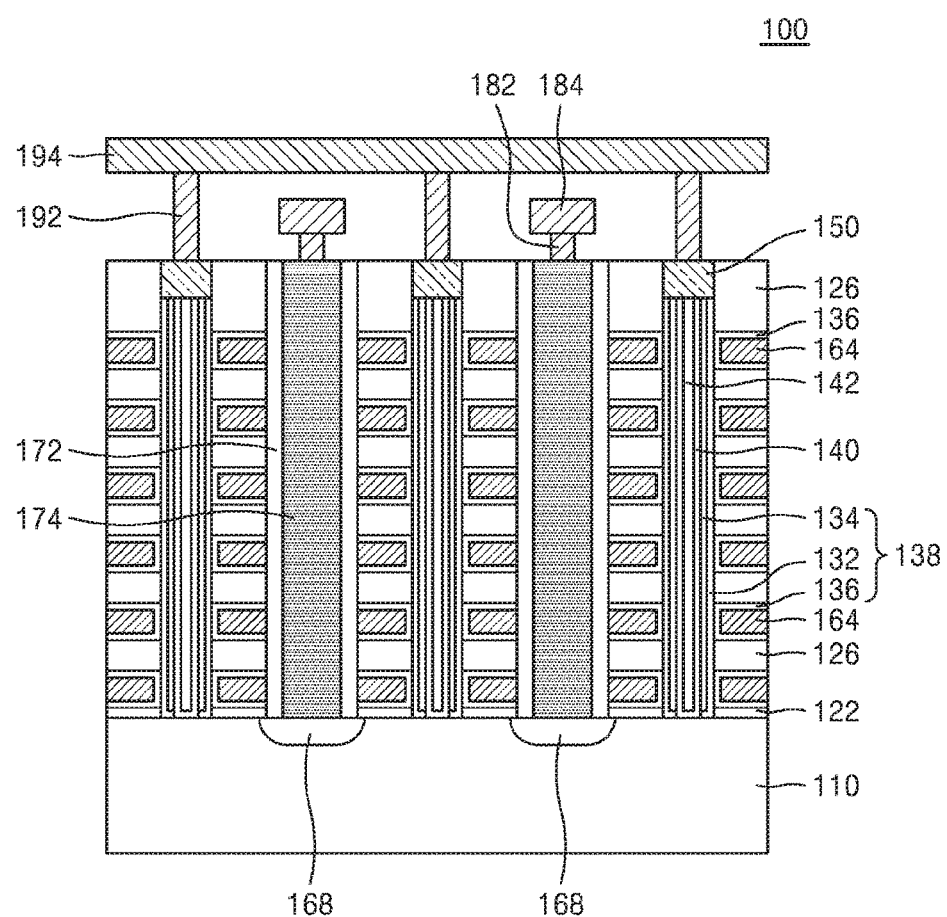

Referring to FIG. 3H, an insulating spacer 172 is formed on an inner sidewall of each of the plurality of openings 160, and a conductive plug 174 fills an inner space of each of the plurality of openings 160.

In example embodiments, the insulating spacer 172 may include a silicon oxide film, a silicon nitride film, or combinations thereof. The conductive plug 174 may include a second conductive barrier film contacting the insulating spacer 172, and a second conductive film filling a space surrounded by the second conductive barrier film in each of the plurality of openings 160. The second conductive barrier film may include a conductive metal nitride, for example, TiN or TaN. The second conductive film may include a metal, for example, tungsten.

A plurality of first contacts 182 may be formed on a plurality of conductive plugs 174, and a plurality of first conductive layers 184 may be formed on the plurality of first contacts 182, respectively. Each of the plurality of first contacts 182 and the plurality of first conductive layers 184 may include a metal, a metal nitride, or combinations thereof.

A plurality of second contacts 192 and a plurality of bit lines 194 may be formed on a plurality of conductive patterns 150. Each of the plurality of second contacts 192 and the plurality of bit lines 194 may include a metal, a metal nitride, or combinations thereof.

According to the method of fabricating the integrated circuit device 100, which has been described with reference to FIGS. 3A to 3H, the aluminum heterocyclic compound according to example embodiments of the inventive concepts is used in the ALD process for forming the blocking insulating film 136 including aluminum oxide, thereby securing properties required as a raw material compound upon the ALD process, for example, relatively high thermal stability, relatively low melting point, relatively high vapor pressure, transportability in a liquid state, ease of vaporization, etc. Therefore, the blocking insulating film 136 having desirable properties may be more easily formed using the aluminum heterocyclic compound according to example embodiments of the inventive concepts. In addition, the blocking insulating film 136 having uniform step coverage along the depths of holes having relatively high aspect ratios may be obtained.

Figure 4A:
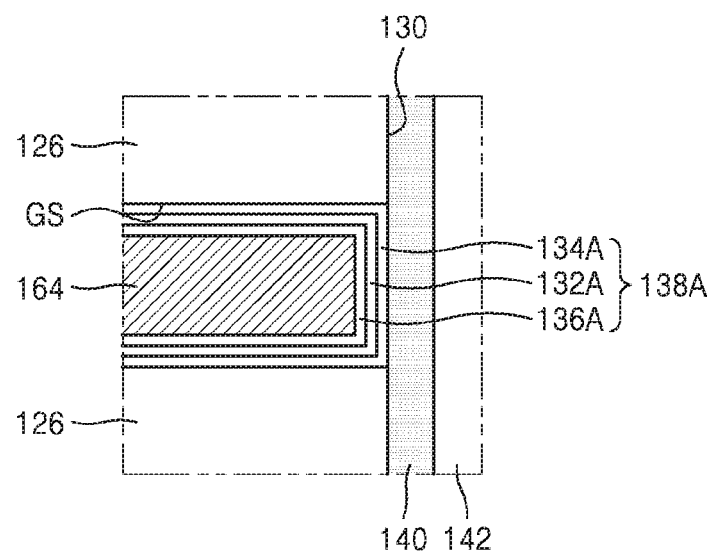
FIGS. 4A to 4C are cross-sectional views showing example structures of other gate dielectric films capable of being used instead of a gate dielectric film shown in FIGS. 3G and 3H.
Figure 4B:
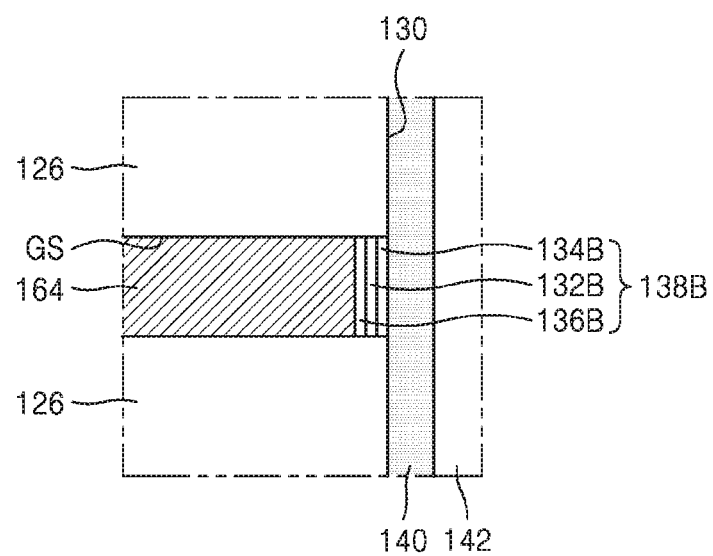
Figure 4C:
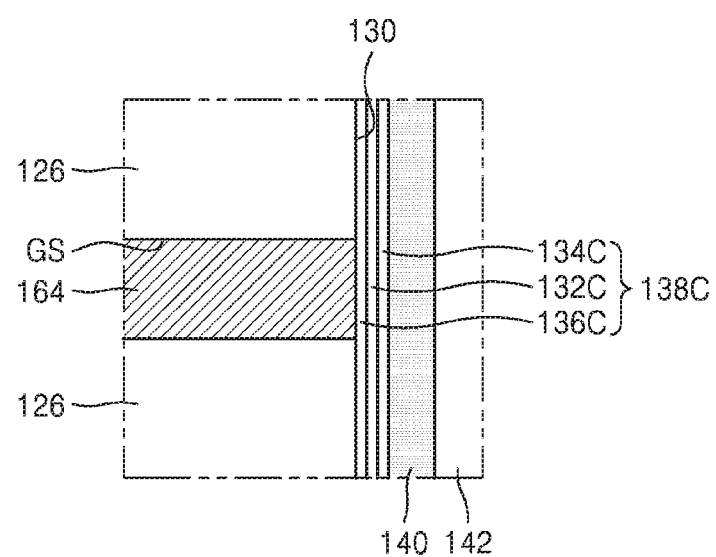

FIGS. 4A to 4C are cross-sectional view illustrating example structures of other gate dielectric films 138A, 138B, and 138C, which may be used instead of the gate dielectric film 138 shown in FIGS. 3G and 3H in the method of fabricating the integrated circuit device 100, the method having been described with reference to FIGS. 3A to 3H.

In example embodiments, the integrated circuit device 100 shown in FIG. 3H may include a gate dielectric film 138A shown in FIG. 4A instead of the gate dielectric film 138. The gate dielectric film 138A may be formed in a gate space GS and cover a surface of the gate electrode 164, which faces the channel region 140, and surfaces of the gate electrode 164, which face the insulating layers 126. The gate dielectric film 138A may include a tunnel dielectric film 134A, a charge storage film 132A, and a blocking insulating film 136A, which are formed on the channel region 140 in this stated order and formed in a portion of the gate space GS between the channel region 140 and the gate electrode 164. The blocking insulating film 136A may be formed by the same method of forming the blocking insulating film 136 described with reference to FIG. 3F.

In example embodiments, the integrated circuit device 100 shown in FIG. 3H may include a gate dielectric film 138B shown in FIG. 4B instead of the gate dielectric film 138. The gate dielectric film 138B may be interposed in a portion of a gate space GS between the channel region 140 and the gate electrode 164 and cover a surface of the gate electrode 164, which faces the channel region 140. The gate dielectric film 138B may include a tunnel dielectric film 134B, a charge storage film 132B, and a blocking insulating film 136B, which are formed on the channel region 140 in this stated order and formed between the channel region 140 and the gate electrode 164. The blocking insulating film 136B may be formed by the same method of forming the blocking insulating film 136 described with reference to FIG. 3F.

In example embodiments, the integrated circuit device 100 shown in FIG. 3H may include the gate dielectric film 138C shown in FIG. 4C instead of the gate dielectric film 138. The gate dielectric film 138C may be between the gate electrode 164 and the channel region 140 to cover a surface of the gate electrode 164, which faces the channel region 140, and may extend parallel to the channel region 140 in a channel hole 130 along a length direction of the channel region 140. The gate dielectric film 138C may include a tunnel dielectric film 134C, a charge storage film 132C, and a blocking insulating film 136C, which are formed on the channel region 140 in this stated order and formed in a portion of an inside of the channel hole 130 between the channel region 140 and the gate electrode 164. The blocking insulating film 136C may be formed by the same method of forming the blocking insulating film 136 described with reference to FIG. 3F.

Descriptions of the tunnel dielectric films 134A, 134B, and 134C, the charge storage films 132A, 132B, and the blocking insulating films 136A, 136B, and 136C, which are shown in FIGS. 4A to 4C, are substantially the same as the descriptions of the tunnel dielectric film 134, the charge storage film 132, and the blocking insulating film 136, which have been described with reference to FIGS. 3A to 3H.

FIGS. 5A to 5J are cross-sectional views illustrating sequential processes of fabricating an integrated circuit device 200 (see FIG. 5J), according to example embodiments of the inventive concepts.

Figure 5A:
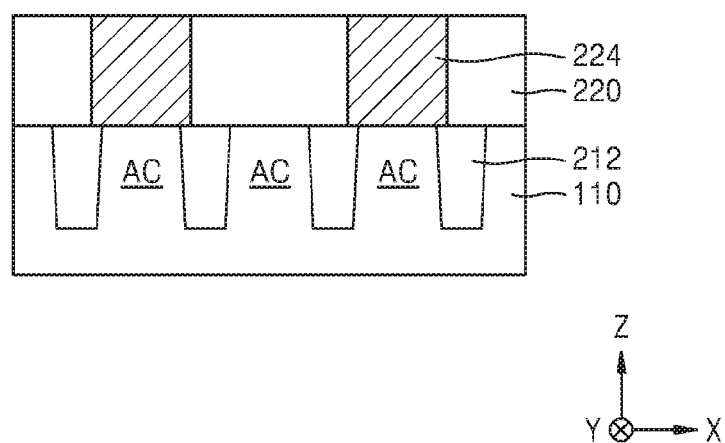
FIGS. 5A to 5J are cross-sectional views illustrating sequential processes of fabricating an integrated circuit device, according to example embodiments of the inventive concepts.

Referring to FIG. 5A, an interlayer dielectric 220 is formed on a substrate 110 including a plurality of active regions AC, followed by forming a plurality of conductive regions 224, which penetrate the interlayer dielectric 220 and are respectively connected to the plurality of active regions AC.

The plurality of active regions AC may be defined by a plurality of device isolation regions 212. The interlayer dielectric 220 may include a silicon oxide film. The plurality of conductive regions 224 may include polysilicon, a metal, a conductive metal nitride, a metal silicide, or combinations thereof.

Figure 5B:
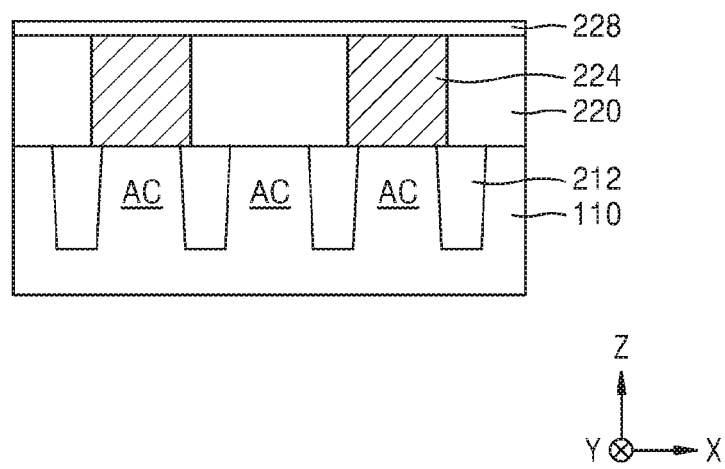

Referring to FIG. 5B, an insulating layer 228 is formed and covers the interlayer dielectric 220 and the plurality of conductive regions 224.

The insulating layer 228 may be used as an etch stop layer. The insulating layer 228 may include an insulating material having etch selectivity with respect to the interlayer dielectric 220 and a mold film 230 (see FIG. 5C) that is formed in a subsequent process. In example embodiments, the insulating layer 228 may include silicon nitride, silicon oxynitride, or combinations thereof.

Figure 5C:
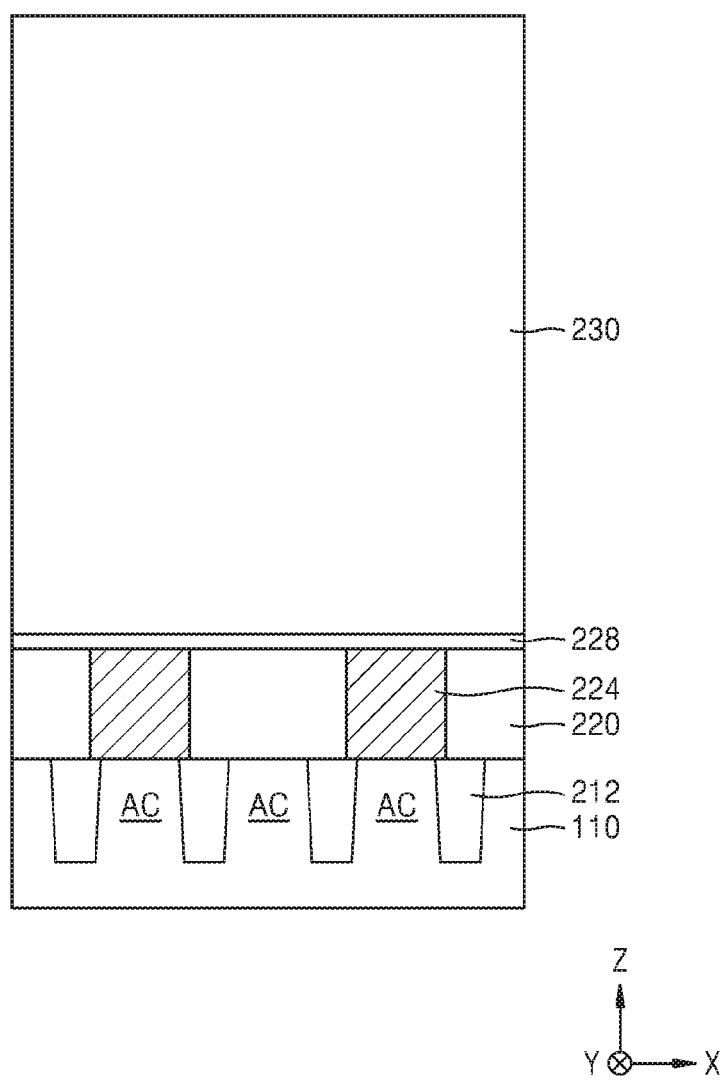

Referring to FIG. 5C, the mold film 230 is formed on the insulating layer 228. The mold film 230 may include an oxide film. In example embodiments, the mold film 230 may include a support film (not shown). The support film may include a material having etch selectivity with respect to the mold film 230.

Figure 5D:
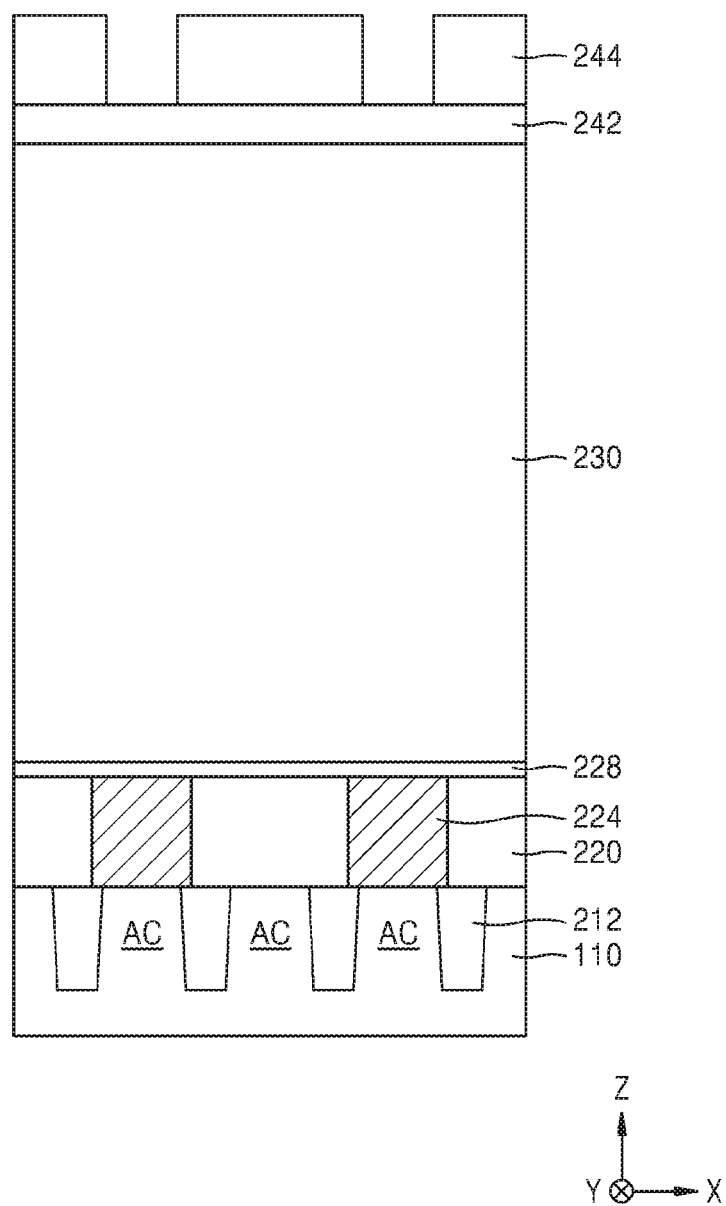

Referring to FIG. 5D, a sacrificial film 242 and a mask pattern 244 are formed on the mold film 230 in this stated order.

The sacrificial film 242 may include an oxide film. The sacrificial film 242 may protect the support film included in the mold film 230. The mask pattern 244 may include an oxide film, a nitride film, a polysilicon film, a photoresist film, or combinations thereof. A region, in which a lower electrode of a capacitor is to be formed, may be defined by the mask pattern 244.

Figure 5E:
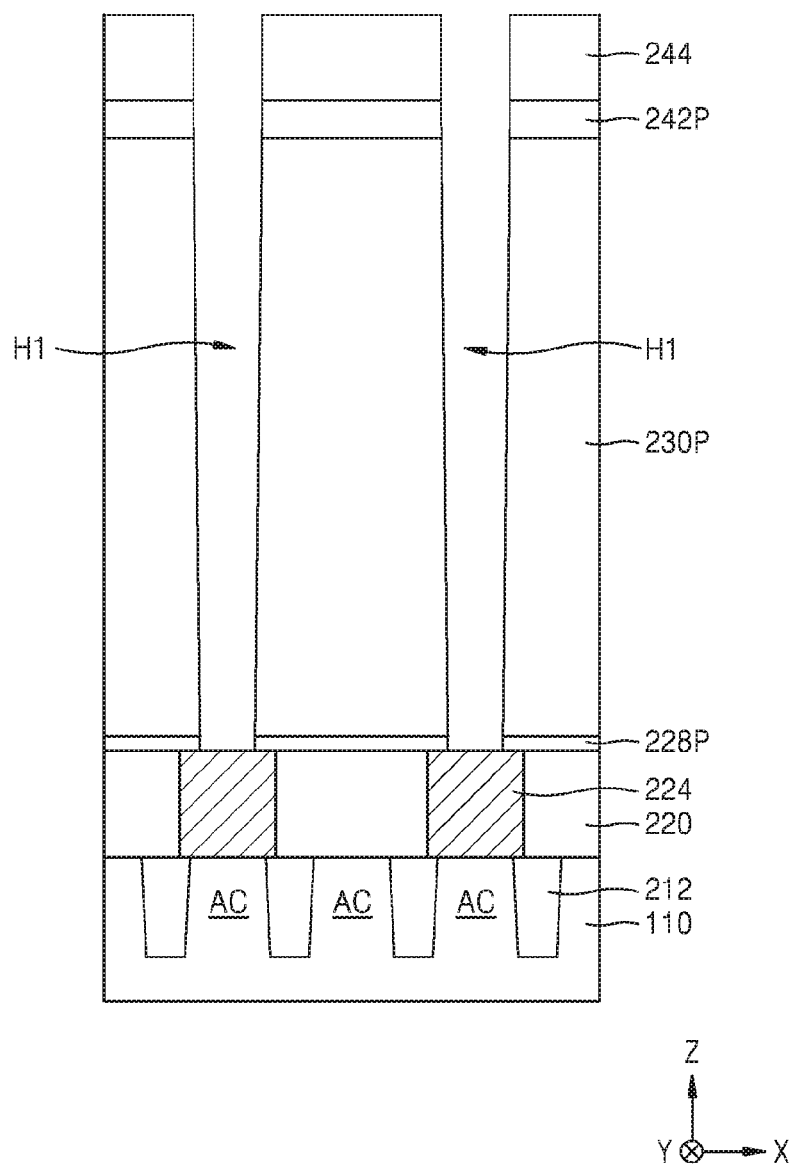

Referring to FIG. 5E, the sacrificial film 242 and the mold film 230 are dry-etched using the mask pattern 244 as an etch mask and using the insulating layer 228 as an etch stop layer, thereby forming a sacrificial pattern 242P and a mold pattern 230P, which define a plurality of holes H1. Here, the insulating layer 228 may also be etched due to over-etch, whereby an insulating pattern 228P may be formed and expose the plurality of conductive regions 224.

Figure 5F:
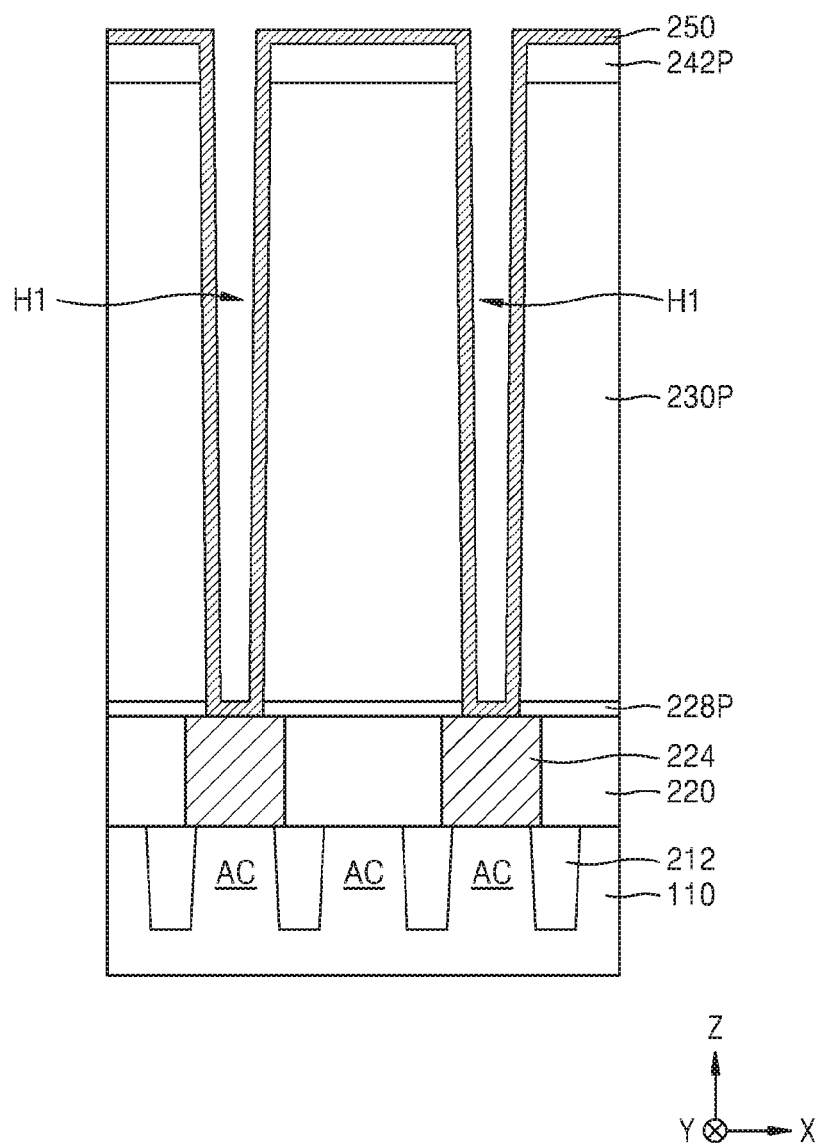

Referring to FIG. 5F, the mask pattern 244 is removed from the resultant of FIG. 5E, followed by forming a lower electrode-forming conductive film 250, which covers an inner sidewall of each of the plurality of holes H1, an exposed surface of the insulating pattern 228P, an exposed surface of each of the plurality of conductive regions 224 inside the plurality of holes H1, and an exposed surface of the sacrificial pattern 242P.

The lower electrode-forming conductive film 250 may be conformally formed on the sidewalls of the plurality of holes H1 such that an inner space of each of the plurality of holes H1 partially remains.

The lower electrode-forming conductive film 250 may include a doped semiconductor, a conductive metal nitride, a metal, a metal silicide, a conductive oxide, or combinations thereof. For example, the lower electrode-forming conductive film 250 may include TiN, TiAlN, TaN, TaAlN, W, WN, Ru, $RuO_2$, $SrRuO_3$, Ir, $IrO_2$, Pt, PtO, BSRO((Ba,Sr)$RuO_3$), CRO(Ca$RuO_3$), LSCO((La,Sr)$CoO_3$), or combinations thereof. To form lower electrode-forming conductive film 250, a CVD, metal organic CVD (MOCVD), or ALD process may be used.

Figure 5G:
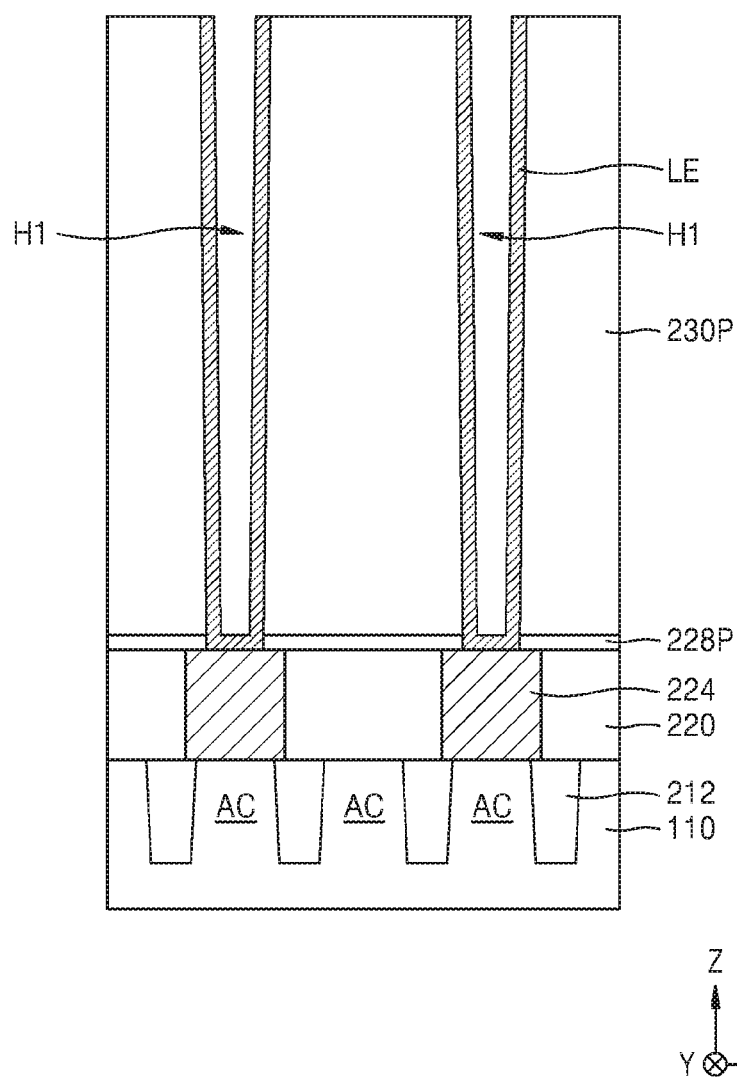

Referring to FIG. 5G, an upper side of the lower electrode-forming conductive film 250 is partially removed, thereby dividing the lower electrode-forming conductive film 250 into a plurality of lower electrodes LE.

To form the plurality of lower electrodes LE, a portion of the upper side of the lower electrode-forming conductive film 250 and the sacrificial pattern 242P (see FIG. 5F) may be removed using an etchback or chemical mechanical polishing (CMP) process such that a top surface of the mold pattern 230P is exposed.

Figure 5H:
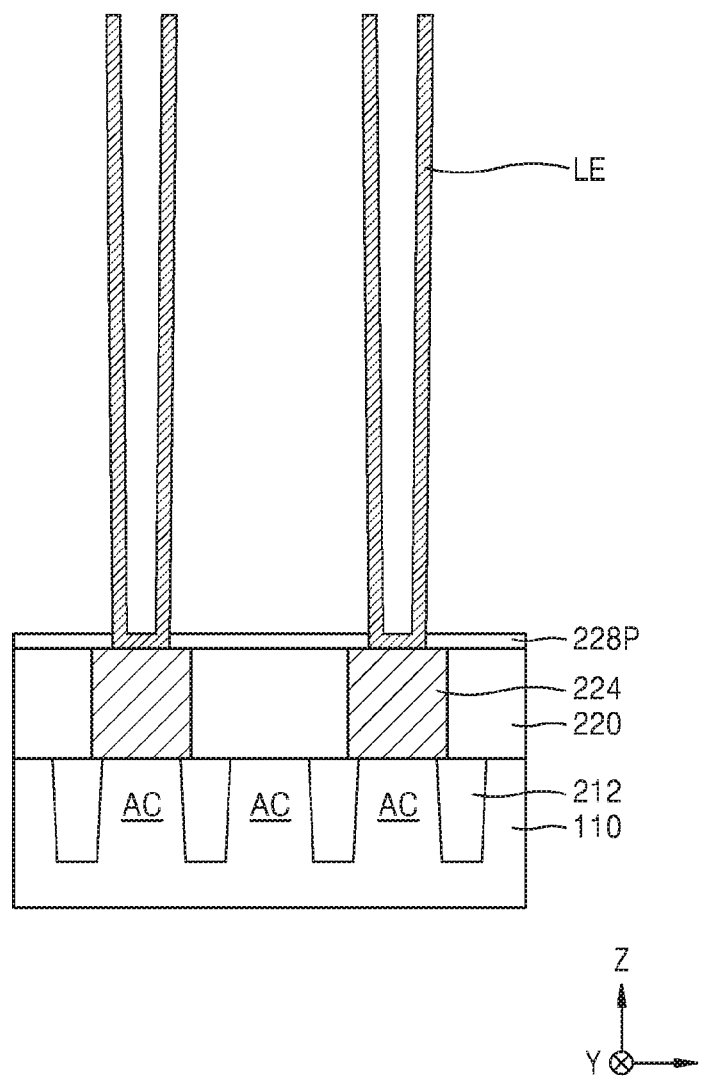

Referring to FIG. 5H, the mold pattern 230P is removed, thereby exposing outer walls of the plurality of lower electrodes LE having cylindrical shapes.

Figure 5I:
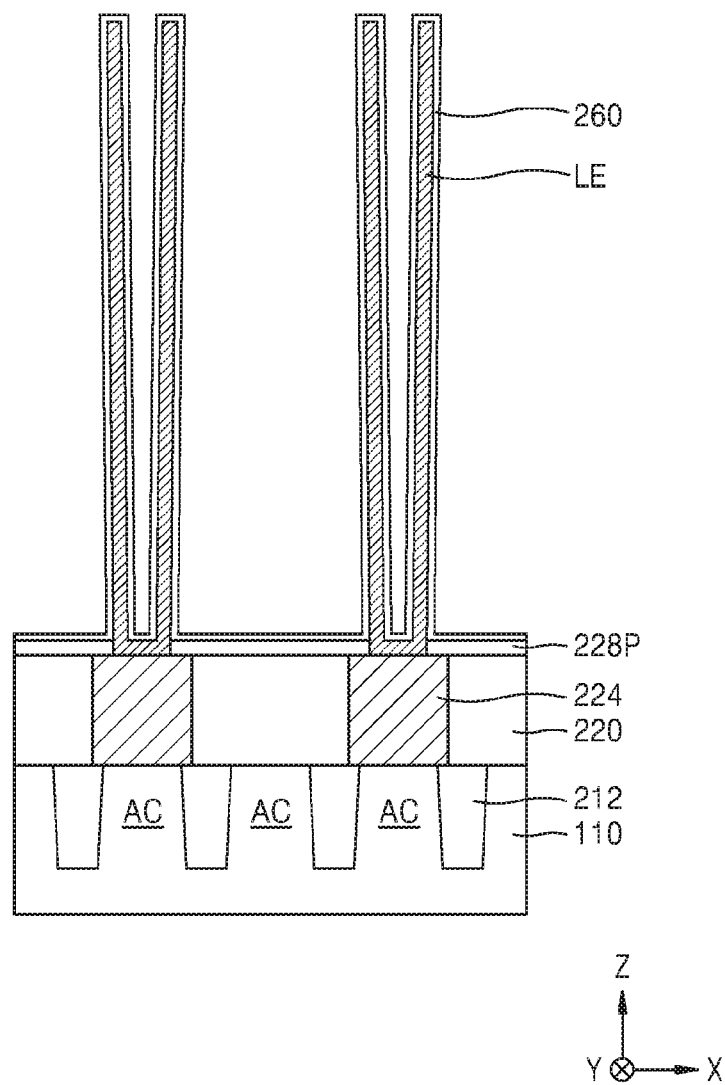

Referring to FIG. 5I, a dielectric film 260 is formed on the plurality of lower electrodes LE.

The dielectric film 260 may conformally cover exposed surfaces of the plurality of lower electrodes LE. The dielectric film 260 may include an aluminum oxide film. The dielectric film 260 may be formed by an ALD process. To form the dielectric film 260, the method of forming a thin film, according to example embodiments of the inventive concepts, may be used, the method having been described with reference to FIG. 1 or 2.

In example embodiments, the dielectric film 260 may include a single layer of an aluminum oxide film. In example embodiments, the dielectric film 260 may include a combination of at least one aluminum oxide film and at least one high-K dielectric film selected from a tantalum oxide film and a zirconium oxide film.

To form an aluminum oxide film constituting the dielectric film 260 by an ALD process, the aluminum heterocyclic compound represented by Chemical Formula (I), for example, the aluminum heterocyclic compound represented by Chemical Formula (1), may be used as an Al source. The ALD process for forming the dielectric film 260 may be performed at about 300° C. to about 600° C. After the formation of the dielectric film 260, the dielectric film 260 may be annealed at a temperature of about 500° C. to about 1150° C.

Figure 5J:
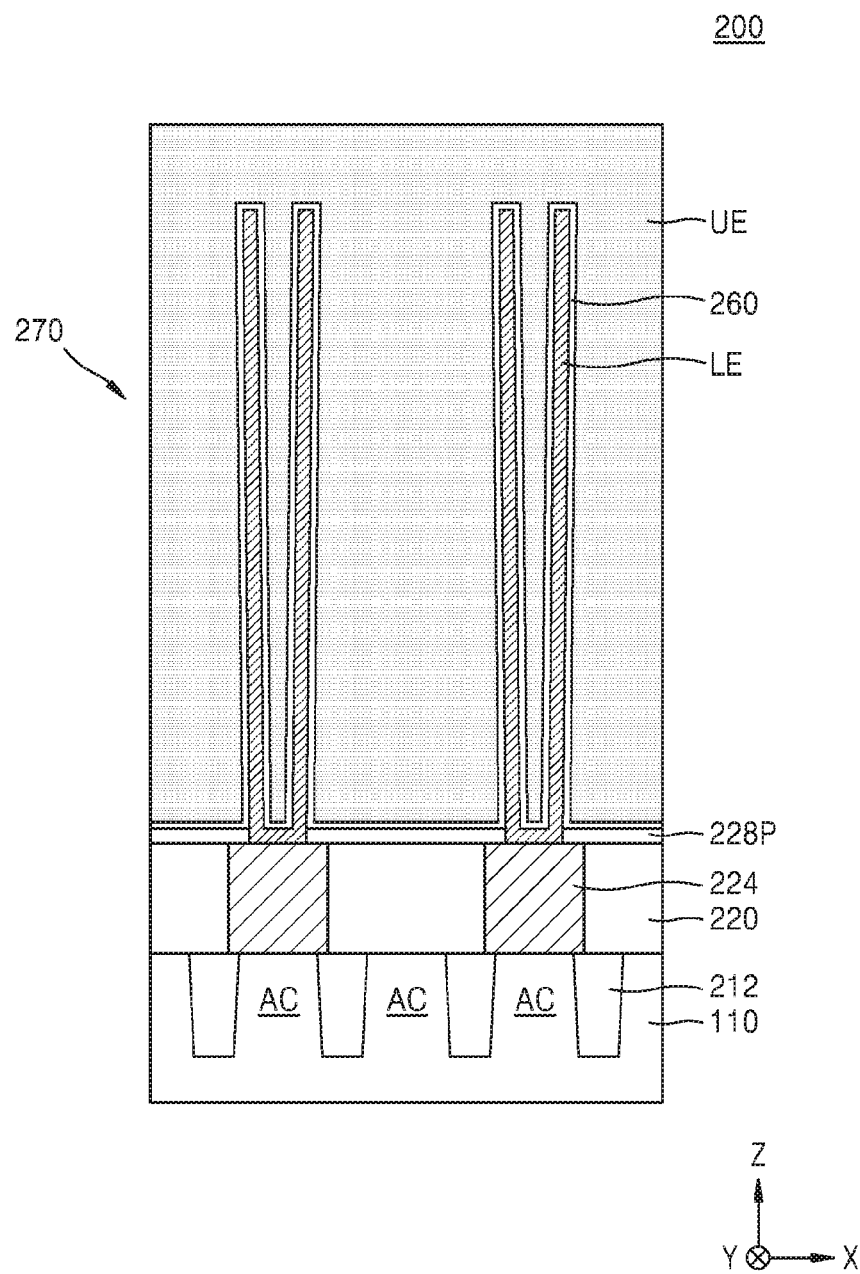

Referring to FIG. 5J, an upper electrode UE is formed on the dielectric film 260. The lower electrode LE, the dielectric film 260, and the upper electrode UE may constitute a capacitor 270.

The upper electrode UE may include a doped semiconductor, a conductive metal nitride, a metal, a metal silicide, a conductive oxide, or combinations thereof. To form the upper electrode UE, a CVD, MOCVD, PVD, or ALD process may be used.

In the method of fabricating the integrated circuit device 200, which has been described with reference to FIGS. 5A to 5J, a pillar-type lower electrode having no inner space may be formed instead of the cylindrical lower electrode LE, and the dielectric film 260 may be formed on the pillar-type lower electrode.

In the method of fabricating the integrated circuit device 200, which has been described with reference to FIGS. 5A to 5J, the capacitor 270 includes the lower electrode LE having a 3-dimensional electrode structure in order to increase capacitance of the capacitor 270. To compensate for reduction in capacitance due to reduction of a design rule, an aspect ratio of the 3-dimensional structured lower electrode LE is increased. According to the method of fabricating the integrated circuit device 200, when the dielectric film 260 is formed on the lower electrode LE by an ALD process, the aluminum heterocyclic compound required for forming the dielectric film 260 may be easily delivered up to a lower portion of a 3-dimensional structure having a relatively high aspect ratio. Therefore, the dielectric film 260 exhibiting improved step coverage may be formed on the lower electrode LE having a relatively high aspect ratio.

FIGS. 6A to 6D are cross-sectional views illustrating sequential processes of fabricating an integrated circuit device 300 (see FIG. 6D), according to example embodiments of the inventive concepts.

Figure 6A:
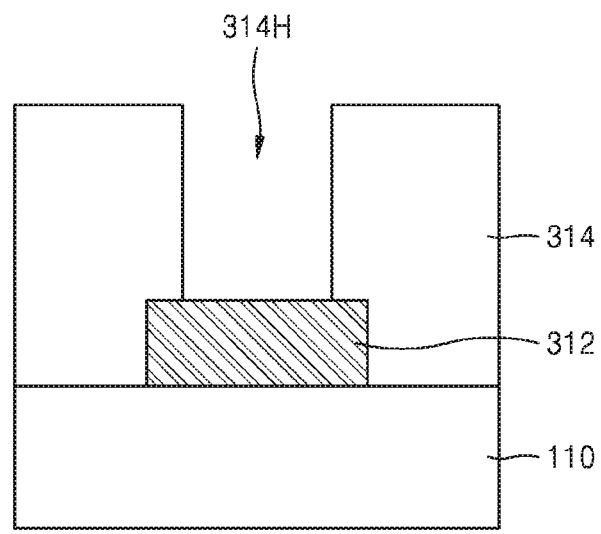
FIGS. 6A to 6D are cross-sectional views illustrating sequential processes of fabricating an integrated circuit device, according to example embodiments of the inventive concepts.

Referring to FIG. 6A, a conductive pattern 312 is formed on a substrate 110, and an interlayer dielectric pattern 314 having a hole 314H is formed on the conductive pattern 312. A portion of the conductive pattern 312 may be exposed by the hole 314H.

The conductive pattern 312 may be a source/drain region, a gate electrode, or a wiring layer. The interlayer dielectric pattern 314 may include a single layer or multiple layers including a silicon oxide film, a silicon nitride film, or combinations thereof.

Figure 6B:
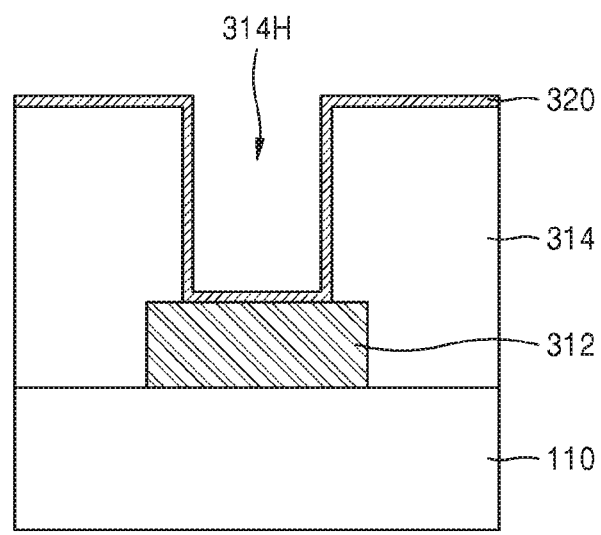

Referring to FIG. 6B, a conductive barrier film 320 is formed on an exposed surface of the conductive pattern 312 and an exposed surface of the interlayer dielectric pattern 314 and covers an inner wall of the hole 314H.

The conductive barrier film 320 may include an aluminum nitride film. To form the conductive barrier film 320, an ALD process may be used. To form the conductive barrier film 320, the method of forming a thin film, according to example embodiments of the inventive concepts, may be used, the method having been described with reference to FIG. 1 or 2. To form an aluminum nitride film constituting the conductive barrier film 320 by an ALD process, the aluminum heterocyclic compound represented by Chemical Formula (I), for example, the aluminum heterocyclic compound represented by Chemical Formula (1), may be used as an Al source. The ALD process for forming the conductive barrier film 320 may be performed at about 300° C. to about 600° C. After the formation of the conductive barrier film 320, the conductive barrier film 320 may be annealed at a temperature of about 500° C. to about 1150° C.

Figure 6C:
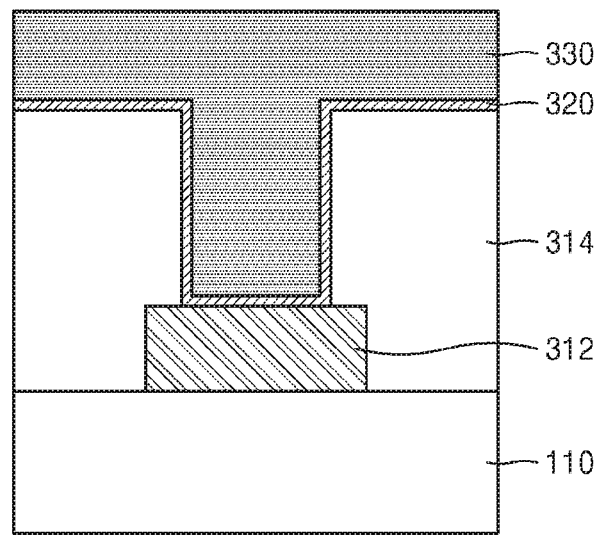

Referring to FIG. 6C, a wiring layer 330 is formed on the conductive barrier film 320, the wiring layer 330 having a sufficient thickness to fill the hole 314H (see FIG. 6B).

The wiring layer 330 may include a metal, for example, tungsten or copper.

Figure 6D:
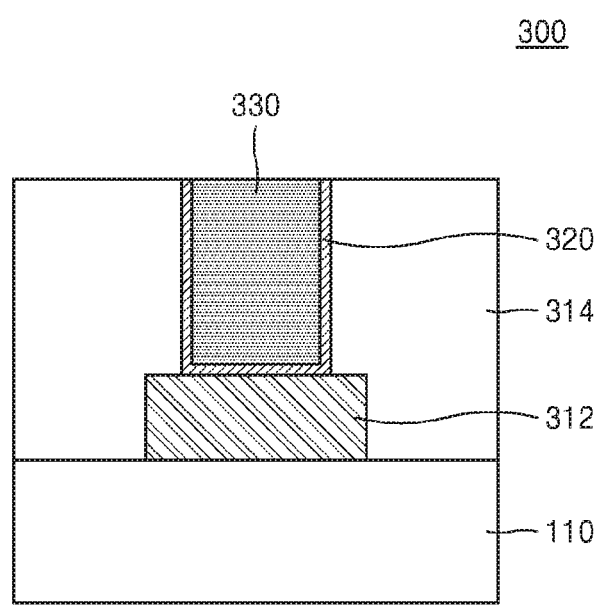

Referring to FIG. 6D, undesirable portions of the conductive barrier film 320 and the wiring layer 330 are removed using etchback, CMP, or combinations thereof, whereby the conductive barrier film 320 and the wiring layer 330 remain in the hole 314H (see FIG. 6B).

According to the method of fabricating the integrated circuit device 300, which has been described with reference to FIGS. 6A to 6D, the conductive barrier film 320 having improved film quality is provided by reducing amounts of impurities in the aluminum nitride film constituting the conductive barrier film 320, thereby improving the reliability of the integrated circuit device 300.

Figure 7A:
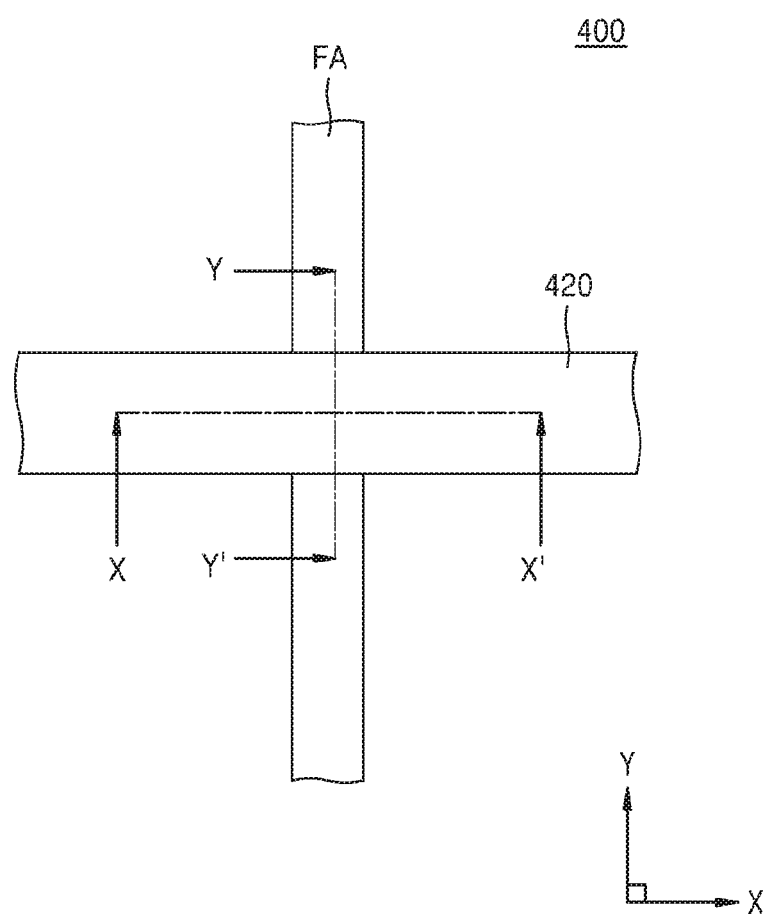
FIGS. 7A to 7C are diagrams for explaining a method of fabricating an integrated circuit device, according to example embodiments of the inventive concepts, and in particular.
Figure 7B:
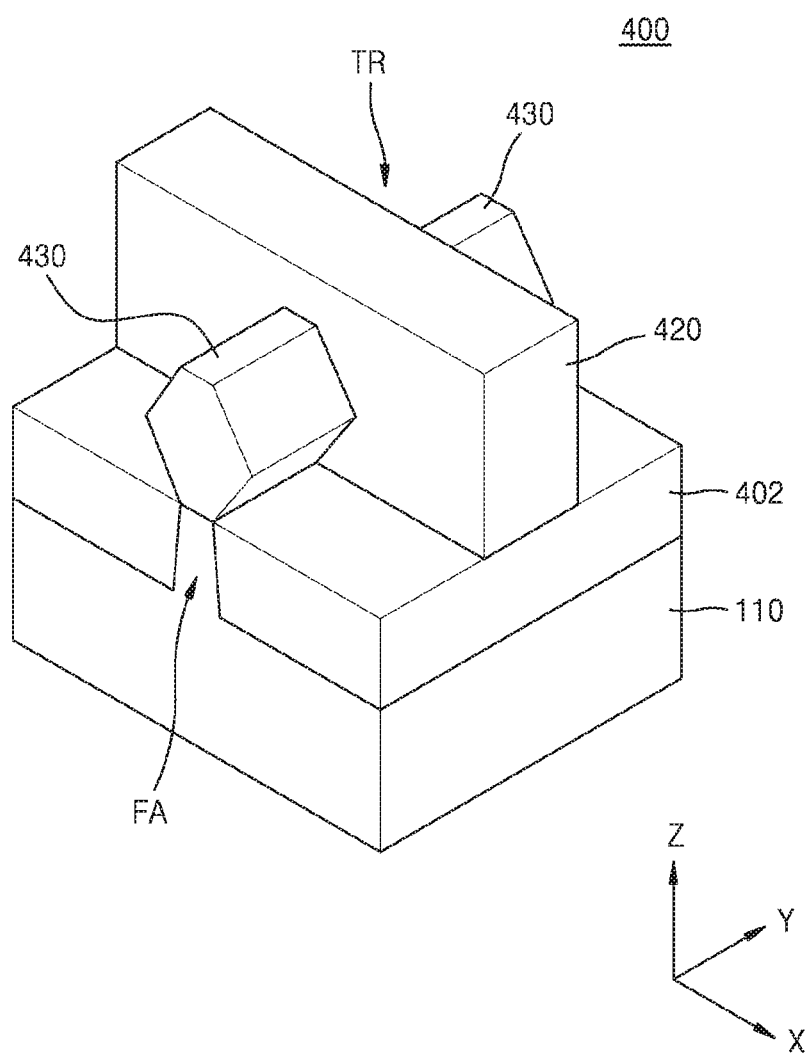
Figure 7C:
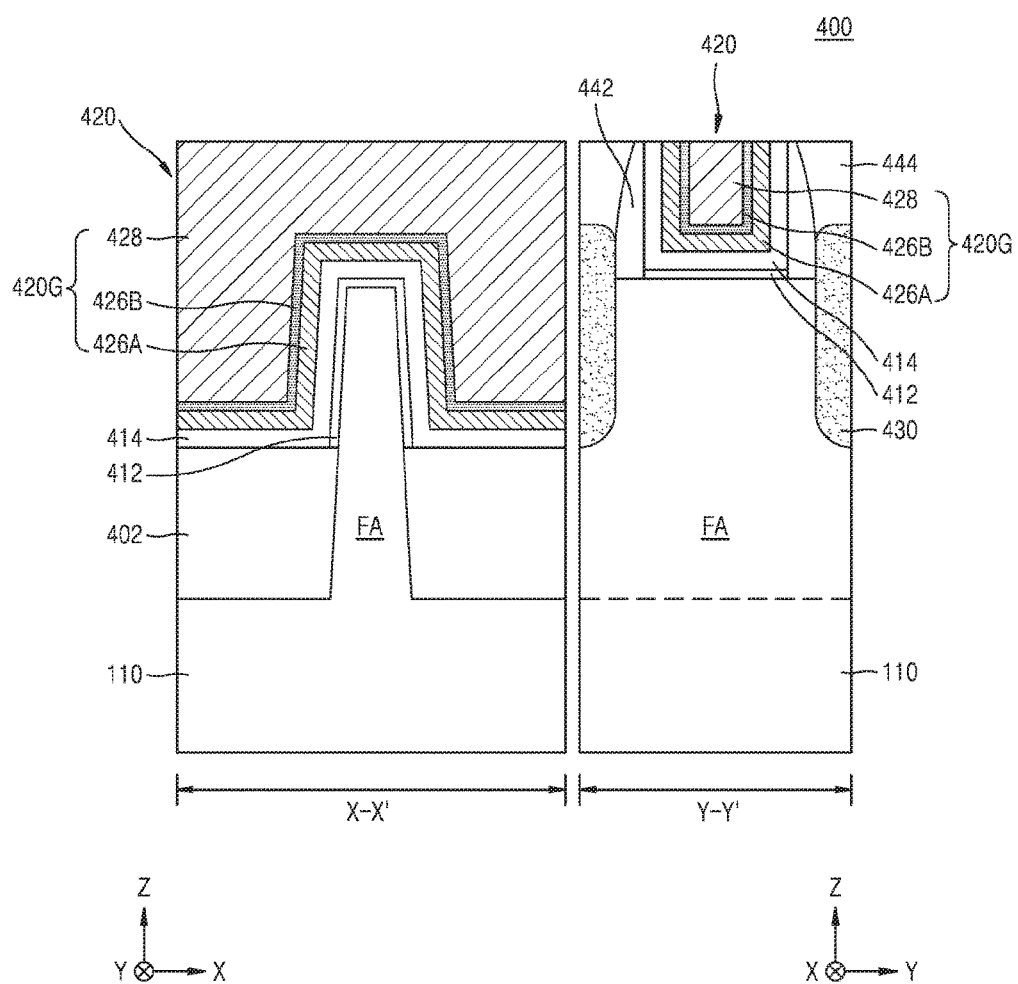

FIGS. 7A to 7C are diagrams for explaining a method of fabricating an integrated circuit device, according to example embodiments of the inventive concepts, and in particular, FIG. 7A is a plan view of an integrated circuit device 400, FIG. 7B is a perspective view of the integrated circuit device 400 of FIG. 7A, and FIG. 7C shows cross-sectional views of the integrated circuit device 400, which are respectively taken along lines X-X' and Y-Y' of FIG. 7A.

Referring to FIGS. 7A to 7C, the integrated circuit device 400 includes a fin-type active region FA protruding from a substrate 110.

The fin-type active region FA may extend along one direction (Y direction in FIGS. 7A and 7B). A device isolation film 402 is formed on the substrate 110 and covers a lower sidewall of the fin-type active region FA. The fin-type active region FA protrudes in a fin shape upwards from the device isolation film 402. In example embodiments, the device isolation film 402 may include a silicon oxide film, a silicon nitride film, a silicon oxynitride film, or combinations thereof.

On the fin-type active region FA on the substrate 110, a gate structure 420 may extend in a direction (X direction) intersecting the extension direction of the fin-type active region FA. A pair of source/drain regions 430 may be formed in the fin-type active region FA at both sides of the gate structure 420.

The pair of source/drain regions 430 may include a semiconductor layer epitaxially grown on the fin-type active region FA. Each of the pair of source/drain regions 430 may include an embedded SiGe structure including a plurality of epitaxially grown SiGe layers, an epitaxially grown Si layer, or an epitaxially grown SiC layer. The pair of source/drain regions 430 are not limited to an example shape shown in FIG. 7B, and may have various shapes.

A MOS transistor TR may be formed at an intersection of the fin-type active region FA and the gate structure 420. The MOS transistor TR may include a 3-dimensional structured MOS transistor in which channels are formed on a top surface and both side surfaces of the fin-type active region FA. The MOS transistor TR may constitute an NMOS transistor or a PMOS transistor.

As shown in FIG. 7C, the gate structure 420 may include an interfacial layer 412, a high-K dielectric film 414, a first metal-containing layer 426A, a second metal-containing layer 426B, and a gap-fill metal layer 428, which are formed on a surface of the fin-type active region FA in this stated order. The first metal-containing layer 426A, the second metal-containing layer 426B, and the gap-fill metal layer 428 of the gate structure 420 may constitute a gate electrode 420G.

An insulating spacer 442 may be formed on both side surfaces of the gate structure 420. The insulating spacer 442 is covered with an interlayer dielectric 444. The interfacial layer 412 may cover a surface of the fin-type active region FA and may include an insulating material, e.g., an oxide film, a nitride film, or an oxynitride film. The high-K dielectric film 414 may include a material having a higher dielectric constant than a silicon oxide film. For example, the high-K dielectric film 414 may have a dielectric constant of about 10 to about 25. The high-K dielectric film 414 may include a metal oxide or a metal oxynitride.

The first metal-containing layer 426A may include a P-type work function conductive material, for example, TiN. The second metal-containing layer 426B may include an N-type work function conductive material, for example, an N-type metal-containing layer that is required for an NMOS transistor including an Al compound containing Ti or Ta. The second metal-containing layer 426B may include an Al-containing film including a carbon atom. For example, the second metal-containing layer 426B may include TiAlC, TiAlCN, TaAlC, TaAlCN, TiAl, TiAlN, TaAlN or combinations thereof.

To form the second metal-containing layer 426B, the method of forming a thin film may be used, the method having been described with reference to FIG. 1 or 2. To form the second metal-containing layer 426B, an ALD process may be used. Here, the aluminum heterocyclic compound represented by Chemical Formula (I), for example, the aluminum heterocyclic compound represented by Chemical Formula (1), may be used as an Al source. The ALD process for forming the second metal-containing layer 426B may be performed at about 300° C. to about 600° C. In example embodiments, after the formation of the second metal-containing layer 426B, the second metal-containing layer 426B may be annealed at a temperature of about 500° C. to about 1150° C.

The second metal-containing layer 426B, in conjunction with the first metal-containing layer 426A, may adjust a work function of the gate structure 420, thereby adjusting a threshold voltage of the gate structure 420.

The gap-fill metal layer 428 may fill a remaining gate space above the second metal-containing layer 426B when the gate structure 420 is formed by a replacement metal gate (RMG) process. If the remaining gate space above the second metal-containing layer 426B is not present after the formation of the second metal-containing layer 426B, the gap-fill metal layer 428 may be omitted instead of being formed on the second metal-containing layer 426B. The gap-fill metal layer 428 may include W, a metal nitride (e.g., TiN or TaN), Al, a metal carbide, a metal silicide, a metal aluminum carbide, a metal aluminum nitride, or a metal silicon nitride.

When the integrated circuit device 400 is fabricated by the method according to example embodiments of the inventive concepts, which has been described with reference to FIGS. 7A to 7C, the aluminum heterocyclic compound according to example embodiments of the inventive concepts is used to form the second metal-containing layer 426B, thereby improving the reliability of the integrated circuit device 400.

Figure 8:
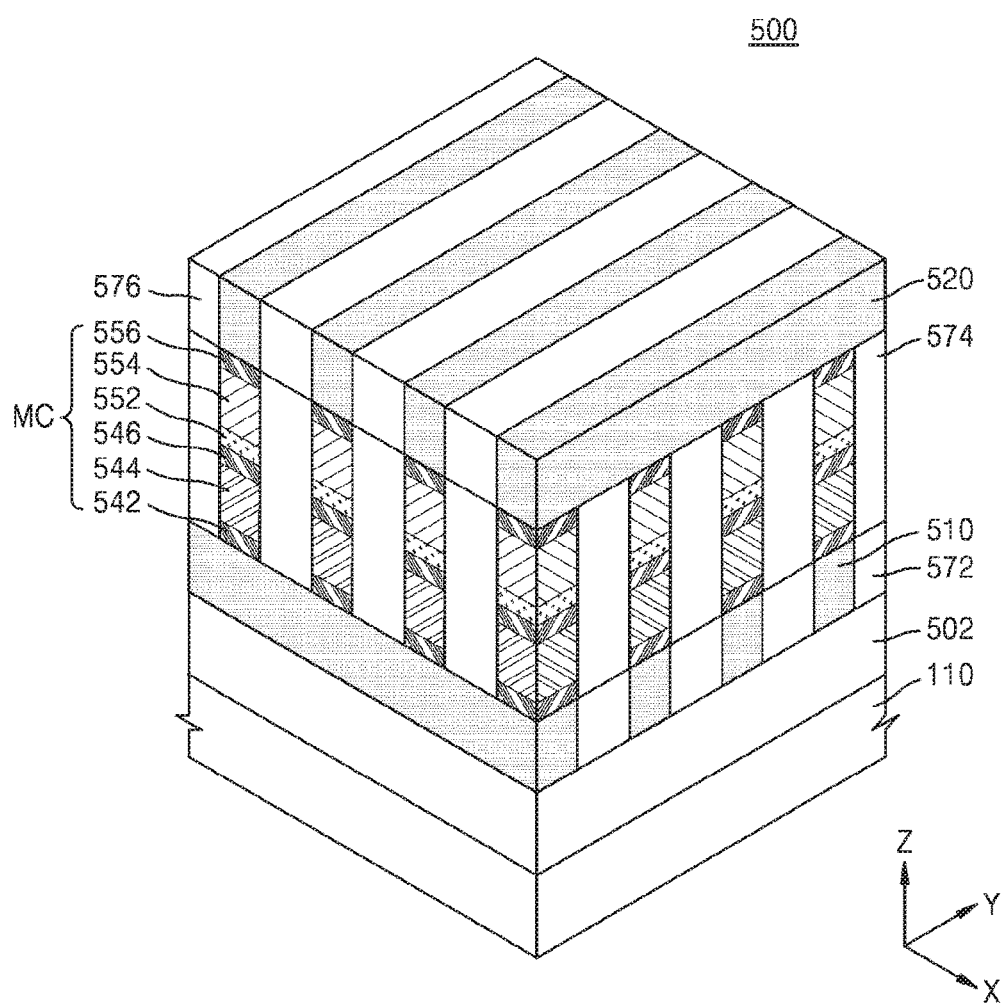
FIG. 8 is a perspective view for explaining a method of fabricating an integrated circuit device, according to example embodiments of the inventive concepts.

FIG. 8 is a perspective view for explaining a method of fabricating an integrated circuit device, according to example embodiments of the inventive concepts. An integrated circuit device 500 shown in FIG. 8 may constitute a resistive memory device.

Referring to FIG. 8, the integrated circuit device 500 may include an interlayer dielectric 502 on a substrate 110 and include a plurality of first electrode lines 510, a plurality of resistive memory cells MC, and a plurality of second electrode lines 520, which are formed on the interlayer dielectric 502 in this stated order.

The interlayer dielectric 502 may include a silicon oxide film, a silicon nitride film, or combinations thereof.

The plurality of first electrode lines 510 may extend parallel to each other on the substrate 110 in a first direction (X direction). The plurality of second electrode lines 520 may extend parallel to each other over the plurality of first electrode lines 510 in a second direction (Y direction) intersecting the first direction. The plurality of first electrode lines 510 may be a plurality of word lines and the plurality of second electrode lines 520 may be a plurality of bit lines, or vice versa.

Each of the plurality of first and second electrode lines 510 and 520 may include a metal, a conductive metal nitride, a conductive metal oxide, or combinations thereof. For example, each of the plurality of first and second electrode lines 510 and 520 may include Al, TiAlN, or combinations thereof. To form the plurality of first and second electrode lines 510 and 520, the method of forming a thin film, which has been described with reference to FIG. 1 or 2, may be used. In example embodiments, to form the plurality of first and second electrode lines 510 and 520, an ALD process may be used. Here, the aluminum heterocyclic compound represented by Chemical Formula (I), for example, the aluminum heterocyclic compound represented by Chemical Formula (1), may be used as an Al source. The ALD process may be performed at a first temperature selected from a range of about 300° C. to about 600° C.

The plurality of first and second electrode lines 510 and 520 may further include a conductive barrier film (not shown). The conductive barrier film may include Ti, TiN, Ta, TaN, or combinations thereof.

The plurality of resistive memory cells MC may be arranged between the plurality of first electrode lines 510 and the plurality of second electrode lines 520 and at intersections of the plurality of first electrode lines 510 and the plurality of second electrode lines 520. The plurality of resistive memory cells MC may be spaced apart from each other in the first direction and the second direction. Each of the plurality of resistive memory cells MC may include a lower electrode layer 542, a selection device layer 544, an intermediate electrode layer 546, a heating electrode layer 552, a resistive layer 554, and an upper electrode layer 556.

The resistive layer 554 may include a phase change material reversibly changing between an amorphous phase and a crystalline phase depending upon heating time. For example, the resistive layer 554 may include a material capable of having a reversible change in phase due to Joule heat and having a change in resistance due to such a phase change, the Joule heat being generated by voltage applied to both ends of the resistive layer 554. Specifically, the phase change material may be in a relatively high resistance state when having an amorphous phase, and may be in a relatively low resistance state when having a crystalline phase. The relatively high resistance state is defined as "0", and the relatively low resistance state is defined as "1", whereby data may be stored in the resistive layer 554. The resistive layer 554 may include a chalcogenide material as the phase change material. For example, the resistive layer 554 may include Ge—Sb-Ts (GST). The resistive layer 554 may further include at least one impurity selected from among boron (B), carbon (C), nitrogen (N), oxygen (O), phosphorus (P), and sulfur (S). A driving current of the integrated circuit device 500 may be changed by the at least one impurity. In addition, the resistive layer 554 may further include a metal. When the resistive layer 554 includes a transition metal oxide, the integrated circuit device 500 may be resistive RAM (ReRAM).

The selection device layer 544 may be a current adjusting layer capable of controlling flow of current. The selection device layer 544 may include a material layer capable of having a change in resistance depending upon the amplitude of voltage applied to both ends of the selection device layer 544. For example, the selection device layer 544 may include an ovonic threshold switching (OTS) material. The selection device layer 544 may include a chalcogenide switching material as the OTS material.

The heating electrode layer 552 may be arranged between the intermediate electrode layer 546 and the resistive layer 554 and contact the resistive layer 554. The heating electrode layer 552 may heat the resistive layer 554, in a set or reset operation. The heating electrode layer 552 may include a high-melting point metal or nitride thereof including TiN, TiSiN, TiAlN, TaSiN, TaAlN, TaN, WSi, WN, TiW, MoN, NbN, TiBN, ZrSiN, WSiN, WBN, ZrAlN, MoAlN, TiAl, TiON, TiAlON, WON, TaON, C, SiC, SiCN, CN, TiCN, TaCN, or combinations thereof.

Each of the lower electrode layer 542, the intermediate electrode layer 546, and the upper electrode layer 556 may include Al, TiAlN, or combinations thereof. At least one of the lower electrode layer 542, the intermediate electrode layer 546, and the upper electrode layer 556 may be formed by the method of forming a thin film, which has been described with reference to FIG. 1 or 2. In example embodiments, to form at least one of the lower electrode layer 542, the intermediate electrode layer 546, and the upper electrode layer 556, an ALD process may be used. Here, the aluminum heterocyclic compound represented by Chemical Formula (I), for example, the aluminum heterocyclic compound represented by Chemical Formula (1), may be used as an Al source. The ALD process may be performed at a first temperature selected from a range of about 300° C. to about 600° C.

A first insulating layer 572 may be arranged between the plurality of first electrode lines 510. A second insulating layer 574 may be arranged between the plurality of resistive memory cells MC. A third insulating layer 576 may be arranged between the plurality of second electrode lines 520.

Hereinafter, the aluminum heterocyclic compound and the method of forming a thin film, according to example embodiments of the inventive concepts, will be explained in more detail with reference to some examples. However, the inventive concepts are not limited to the following examples.

EXAMPLE 1

Synthesis of Aluminum Heterocyclic Compound [(CH$_3$)N(CH$_2$CH$_2$CH$_2$)$_2$Al(CH$_3$)] Represented by Chemical Formula (1)

Methyldichloroaluminum (41 g, 0.37 mol) was melted, followed by adding a solution of 3-magnesiumchloro-N-(3-magnesiumpropyl)-N-methylpropan-1-amine (400 ml, 1 N) in tetrahydrofuran (THF) to methyldichloroaluminum at room temperature. Next, the components were stirred at room temperature for 17 hours. After the completion of the reaction, a solvent and volatile byproducts were removed at reduced pressure, followed by performing vacuum distillation (32° C., 0.54 torr), thereby obtaining 35 g of a compound represented by Chemical Formula (1) (yield 61%).

(Analysis)

$^1$H-NMR (solvent: benzene-d6, ppm) δ −0.51 (3H, S, CH$_3$Al), 0.18 (4H, t, NCH$_2$CH$_2$CH$_2$Al), 1.61 (4H, m, NCH$_2$CH$_2$CH$_2$Al), 1.79 (3H, s, CH$_3$N(CH$_2$CH$_2$CH$_2$)Al), 1.82 (2H, m, NCHH'CH$_2$Al), 2.08 (2H, m, NCHH'CH$_2$Al)

Evaluation

Properties Evaluation of Aluminum Heterocyclic Compound Represented by Chemical Formula (1)

Figure 9:
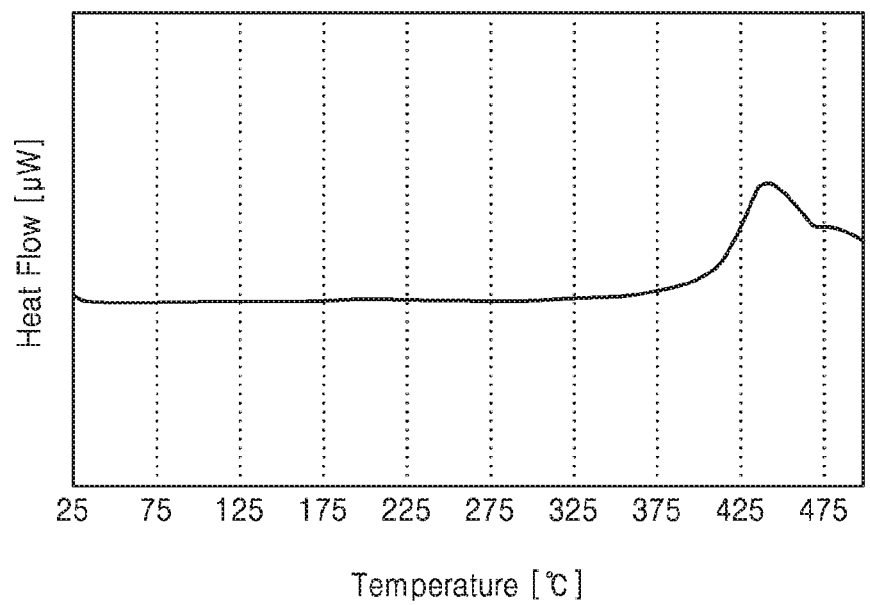
FIG. 9 is a graph depicting results of differential scanning calorimetry (DSC) analysis of the aluminum heterocyclic compound according to example embodiments of the inventive concepts.

FIG. 9 is a graph depicting results of differential scanning calorimetry (DSC) analysis of the aluminum heterocyclic compound represented by Chemical Formula (1) and obtained in Example 1.

As can be seen from the results of FIG. 9, a thermal decomposition peak of the aluminum heterocyclic compound represented by Chemical Formula (1) was not observed up to about 400° C., and it was confirmed that the thermal decomposition of the aluminum heterocyclic compound occurred at about 405° C.

As a comparative example, trimethylaluminum (TMA) was subjected to DSC analysis in the same manner, and as a result, it was confirmed that the thermal decomposition of TMA occurred at about 237° C. From this result, it could be seen that the aluminum heterocyclic compound represented by Chemical Formula (1) had improved thermal stability.

Figure 10:
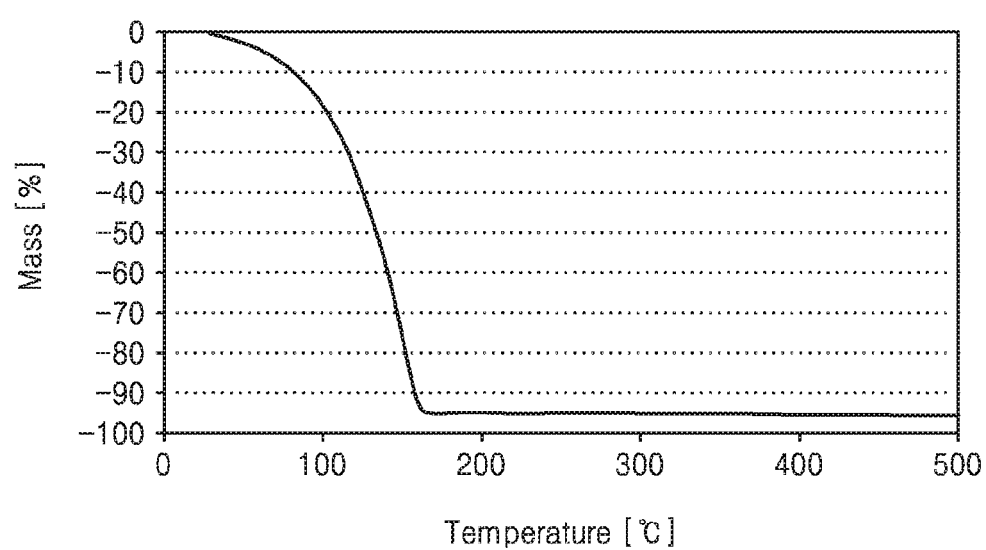
FIG. 10 is a graph depicting results of thermogravimetric analysis (TGA) of the aluminum heterocyclic compound according to example embodiments of the inventive concepts.

FIG. 10 is a graph depicting results obtained by performing thermogravimetric analysis (TGA) of 10 mg of the aluminum heterocyclic compound represented by Chemical Formula (1) at a heating rate of 10° C./min in an argon atmosphere.

FIG. 10 shows weight loss percentage along with temperature for the aluminum heterocyclic compound represented by Chemical Formula (1). As can be seen from FIG. 10, the aluminum heterocyclic compound represented by Chemical Formula (1) exhibited quick vaporization and was vaporized by 99% or more at about 170° C. without residue due to thermal decomposition.

Figure 11:
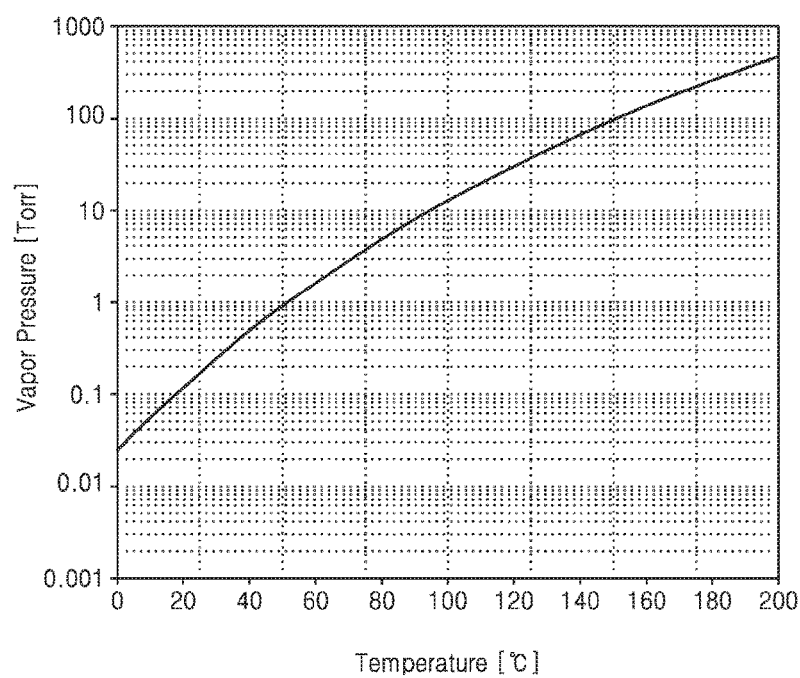
FIG. 11 is a graph depicting measurement results of vapor pressure along with temperature for the aluminum heterocyclic compound according to example embodiments of the inventive concepts.

FIG. 11 is a graph depicting measurement results of vapor pressure along with temperature for the aluminum heterocyclic compound represented by Chemical Formula (1).

From the results of FIG. 11, it was confirmed that the aluminum heterocyclic compound represented by Chemical Formula (1) had a vapor pressure of about 1 Torr at 50° C.

EXAMPLE 2

Formation of Aluminum Oxide Film

An aluminum oxide film was formed on a silicon substrate by an ALD process using the aluminum heterocyclic compound represented by Chemical Formula (1) as a raw material, the aluminum heterocyclic compound being synthesized in Example 1. Here, ozone gas was used as a reactive gas, and argon was used as a purge gas. The substrate was maintained at a temperature of 350° C. to 600° C. during the formation of the aluminum oxide film.

To form the aluminum oxide film, when the following series of processes (1) to (4) was defined as 1 cycle, 200 cycles were repeated.

Process (1): A process of depositing vapor of the aluminum heterocyclic compound onto the substrate maintained at 350° C. to 600° C. by introducing the vapor of the aluminum heterocyclic compound into a reaction chamber for 8 seconds, the vapor of the aluminum heterocyclic compound being obtained by vaporizing the aluminum heterocyclic compound under the condition that a heating temperature of a canister of the aluminum heterocyclic compound was 80° C.

Process (2): A process of removing the unreacted raw material by performing purge for 10 seconds using argon gas supplied at a flow rate of 3000 sccm.

Process (3): A process of performing reaction by introducing ozone gas, which was the reactive gas, into the reaction chamber at a flow rate of 300 sccm for 14 seconds.

Process (4): A process of removing the unreacted raw material by performing purge for 10 seconds using argon gas supplied at a flow rate of 3000 sccm.

Figure 12:
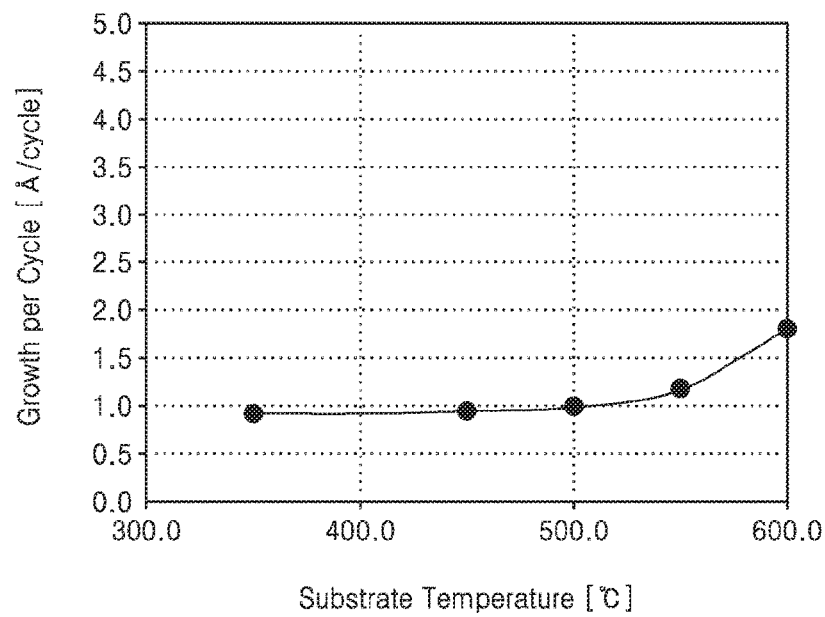
FIG. 12 is a graph depicting measurement results of deposition rate of an aluminum oxide film obtained by the method of forming a thin film according to example embodiments of the inventive concepts.

FIG. 12 is a graph depicting measurement results of deposition rate along with substrate temperature for the aluminum oxide film obtained in Example 2.

According to the results of FIG. 12, the deposition rate at 350° C. to 550° C. ranged from about 0.92 Å/cycle to about 1.17 Å/cycle, and the deposition rate at 600° C. was about 1.81 Å/cycle. From these results, it was confirmed that an ALD window range was from about 350° C. to about 550° C.

From the above results, when the aluminum oxide film was deposited using the aluminum heterocyclic compound represented by Chemical Formula (1), it was confirmed that the aluminum heterocyclic compound showed an ALD behavior allowing a thin film growth rate to be constant and exhibited improved thermal stability, and that a relatively wide ALD window of about 350° C. to about 550° C. could be secured.

Figure 13:
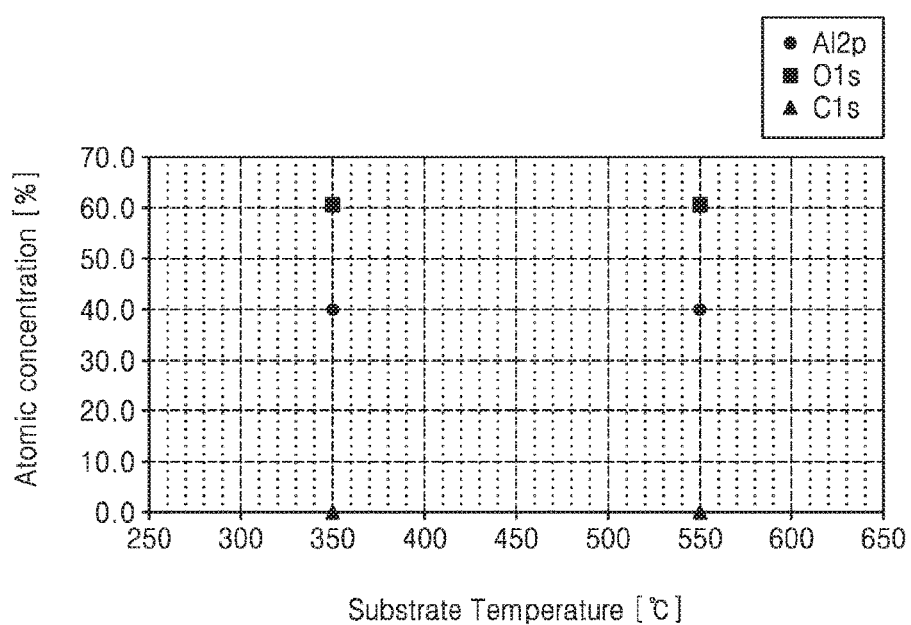
FIG. 13 is a graph depicting X-ray photoelectron spectroscopy (XPS) depth profiling results of the aluminum oxide film obtained by the method of forming a thin film according to example embodiments of the inventive concepts.

FIG. 13 is a graph depicting X-ray photoelectron spectroscopy (XPS) depth profiling results of the aluminum oxide film obtained in Example 2 under the condition that the substrate temperature was maintained at each of 350° C. and 550° C.

When the substrate temperatures were respectively 350° C. and 550° C., it was confirmed that because carbon atoms in the obtained aluminum oxide film were detected in an amount below about 1 atom %, impurities due to the decomposition of a precursor were not generated.

While the inventive concepts have been particularly shown and described with reference to example embodiments thereof, it will be understood that various changes in form and details may be made therein without departing from the spirit and scope of the following claims.

What is claimed is:

1. A method of forming a thin film, the method comprising:
    forming an aluminum oxide film on a substrate using an aluminum compound represented by Chemical Formula (I):

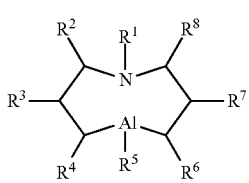

Chemical Formula (I)

wherein each of $R^1$, $R^2$, $R^3$, $R^4$, $R^5$, $R^6$, $R^7$, and $R^8$ are independently a hydrogen atom, a halogen atom, a C1 to C7 substituted or unsubstituted alkyl group, a C2 to C7 substituted or unsubstituted alkenyl group, a C2 to C7 substituted or unsubstituted alkynyl group, or a C4 to C20 substituted or unsubstituted aromatic or alicyclic hydrocarbon group;

wherein the forming includes maintaining the substrate at a temperature from about 350° C. to about 550° C., wherein the forming forms the aluminum oxide film by sequentially supplying the aluminum compound and a reactive gas onto the substrate, the reactive gas including an oxidative gas.

2. The method according to claim 1, wherein the forming forms the aluminum oxide film using the aluminum compound represented by Chemical Formula (II):

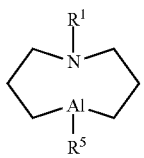

wherein each of R1 and R5 are independently a C1 to C7 alkyl group.

3. The method according to claim 1, wherein the forming supplies the reactive gas including one of $O_2$, $O_3$, plasma $O_2$, $H_2O$, $NO_2$, NO, $N_2O$ (nitrous oxide), $CO_2$, $H_2O_2$, HCOOH, $CH_3COOH$, $(CH_3CO)_2O$, and combinations thereof.

4. The method according to claim 1, wherein the forming further comprises:
vaporizing a source gas including the aluminum compound;
forming an Al source-adsorbed layer on the substrate by supplying the vaporized source gas onto the substrate; and
supplying the reactive gas onto the Al source-adsorbed layer.

5. A method of fabricating an integrated circuit device, the method comprising:
forming a lower structure on a substrate; and
forming an aluminum oxide film on the lower structure by maintaining the substrate at a temperature from about 350° C. to about 550° C. using an aluminum compound represented by Chemical Formula (I):

Chemical Formula (I)

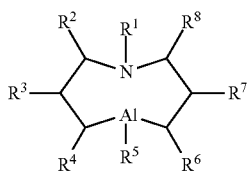

wherein each of $R^1$, $R^2$, $R^3$, $R^4$, $R^5$, $R^6$, $R^7$, and $R^8$ are independently a hydrogen atom, a halogen atom, a C1 to C7 substituted or unsubstituted alkyl group, a C2 to C7 substituted or unsubstituted alkenyl group, a C2 to C7 substituted or unsubstituted alkynyl group, or a C4 to C20 substituted or unsubstituted aromatic or alicyclic hydrocarbon group; and wherein the forming forms the aluminum oxide film by sequentially supplying the aluminum compound and a reactive gas onto the substrate, the reactive gas including an oxidative gas.

6. The method according to claim 5, wherein the forming forms the aluminum oxide film using the aluminum compound represented by Chemical Formula (II):

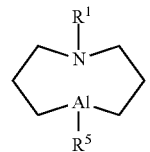

wherein each of R1 and R5 are independently a C1 to C7 alkyl group.

7. The method according to claim 5, wherein the forming a lower structure comprises:
alternately stacking a plurality of insulating layers and a plurality of sacrificial layers on the substrate, the plurality of insulating layers and the plurality of sacrificial layers extending parallel to the substrate;
etching the plurality of sacrificial layers and the plurality of insulating layers to form an opening penetrating the plurality of sacrificial layers and the plurality of insulating layers; and
removing the plurality of sacrificial layers through the opening to form a plurality of gate spaces, each of the gate spaces between two insulating layers among the plurality of insulating layers,
the forming the aluminum oxide film forms the aluminum oxide film in the plurality of gate spaces by supplying the aluminum compound into the plurality of gate spaces through the opening at the temperature of about 350° C. to about 550° C.

8. The method according to claim 7, further comprising:
densifying the aluminum oxide film by annealing the aluminum oxide film at a second temperature that is higher than the temperature after the forming an aluminum oxide film.

* * * * *